(12) United States Patent
Kim et al.

(10) Patent No.: US 11,292,843 B2
(45) Date of Patent: Apr. 5, 2022

(54) ANTI-PD-L1 ANTIBODIES AND METHODS OF USING THE SAME FOR DETECTION OF PD-L1

(71) Applicant: Genentech, Inc., South San Francisco, CA (US)

(72) Inventors: Doris Kim, San Francisco, CA (US); Terence Wong, Alameda, CA (US); Anan Chuntharapai, Colma, CA (US); Cherie Louise Green, Albany, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/885,067

(22) Filed: May 27, 2020

(65) Prior Publication Data

US 2020/0291119 A1    Sep. 17, 2020

Related U.S. Application Data

(63) Continuation of application No. PCT/US2018/062999, filed on Nov. 29, 2018.

(60) Provisional application No. 62/593,125, filed on Nov. 30, 2017.

(51) Int. Cl.
*C07K 16/28* (2006.01)
*G01N 33/574* (2006.01)

(52) U.S. Cl.
CPC ... *C07K 16/2827* (2013.01); *G01N 33/57426* (2013.01); *C07K 2317/33* (2013.01)

(58) Field of Classification Search
None
See application file for complete search history.

(56) References Cited

U.S. PATENT DOCUMENTS

| | | |
|---|---|---|
| 4,275,149 A | 6/1981 | Litman |
| 4,318,980 A | 3/1982 | Boguslaski |
| 4,737,456 A | 4/1988 | Weng |
| 4,816,567 A | 3/1989 | Cabilly |
| 5,316,757 A | 5/1994 | Sherry |
| 5,342,606 A | 8/1994 | Sherry |
| 5,385,893 A | 1/1995 | Kiefer |
| 5,428,139 A | 6/1995 | Kiefer |
| 5,428,155 A | 6/1995 | Sherry |
| 5,462,725 A | 10/1995 | Kiefer |
| 5,480,990 A | 1/1996 | Kiefer |
| 5,648,237 A | 7/1997 | Carter |
| 5,739,294 A | 4/1998 | Kiefer |
| 5,750,660 A | 5/1998 | Kiefer |
| 5,789,199 A | 8/1998 | Pettit et al. |
| 5,834,456 A | 11/1998 | Kiefer |
| 5,840,523 A | 11/1998 | Simmons et al. |
| 5,959,177 A | 9/1999 | Hein et al. |
| 6,040,498 A | 3/2000 | Stomp et al. |
| 6,180,370 B1 * | 1/2001 | Queen ............ C07K 16/2866 435/69.6 |
| 6,372,907 B1 | 4/2002 | Lee |
| 6,417,429 B1 | 7/2002 | Hein et al. |
| 6,420,548 B1 | 7/2002 | Vezina et al. |
| 6,528,624 B1 | 3/2003 | Idusogie |
| 7,125,978 B1 | 10/2006 | Vézina et al. |
| 8,217,149 B2 * | 7/2012 | Irving ............ A61P 31/12 530/387.1 |
| 9,920,123 B2 | 3/2018 | Irving |
| 2010/0203056 A1 | 8/2010 | Irving |
| 2013/0045200 A1 | 2/2013 | Irving |
| 2013/0045201 A1 | 2/2013 | Irving |
| 2013/0045202 A1 | 2/2013 | Irving |
| 2014/0065135 A1 | 3/2014 | Irving |
| 2015/0322153 A1 | 11/2015 | Irving |
| 2016/0222117 A1 | 8/2016 | Irving |
| 2017/0107287 A1 | 4/2017 | Irving |
| 2019/0016807 A1 | 1/2019 | Irving |

FOREIGN PATENT DOCUMENTS

| | | |
|---|---|---|
| WO | 199209690 A2 | 6/1992 |
| WO | 199209690 A3 | 12/1992 |
| WO | 2010077634 A1 | 7/2010 |

OTHER PUBLICATIONS

Lescar, Julien, et al. "Crystal structure of a cross-reaction complex between Fab F9. 13.7 and guinea fowl lysozyme." Journal of Biological Chemistry 270.30 (1995): 18067-18076. (Year: 1995).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
Albert, R. et al. (1998). "Direct Synthesis of [DOTA-DPhe1]-Octreotide and [DOTA-DPhe1, Tyr3]-Octreotide (SMT487): Two Conjugates for Systemic Delivery of Radiotherapeutical Nuclides to Somatostatin Receptor Positive Tumors in Man," Bioorganic & Medicinal Chemistry Letters 8:1207-1210.
Almagro, J. et al. (Jan. 2008), "Humanization of Antibodies," Frontiers in Bioscience 13:1619-1633.

(Continued)

*Primary Examiner* — Michael Szperka
*Assistant Examiner* — Lia E Taylor
(74) *Attorney, Agent, or Firm* — Morrison & Foerster LLP

(57) ABSTRACT

The present application relates to anti-PD-L1 antibodies and their use to detect PD-L1 in a sample from a subject. In some embodiments, the subject has been treated with a therapeutic anti-PD-L1 antibody and an anti-PD-L1 described herein does not compete for binding to PD-L1 with the therapeutic anti-PD-L1 antibody. In some embodiments, the anti-PD-L1 antibody is linked to a N detectable moiety, such as a fluorophore and the anti-PD-L1 antibody is used to detect PD-L1 in a subject using flow cytometry.

68 Claims, 18 Drawing Sheets

Specification includes a Sequence Listing.

(56) References Cited

OTHER PUBLICATIONS

Ausubel, F. et al. (1987). Current Protocols in Molecular Biology, Greene Publishing and Wiley interscience, New York, TOC, 7 pages.

Axworthy, D.B. et al (Feb. 15, 2000). "Cure of Human Carcinoma Xenografts by a Single Dose of Pretargeted Yttrium-90 With Negligible Toxicity," Proc. Natl. Acad. Sci. USA 97(4):1802-1807.

Blend, M.J. et al. (2003). "Labeling anti-HER2/neu Monoclonal Antibodies With 111In and 90Y Using a Bifunctional DTPA Chelating Agent," Cancer Biotherapy & Radiopharmaceuticals 18(3):355-363.

Briggs, M.S.J. et al. (1997). "Synthesis of Functionalised Fluorescent Dyes and Their Coupling to Amines and Amino Acids," J. Chem. Soc., Perkin-Trans. 1:1051-1058.

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Camera, L. et al. (1993). "Evaluation of a New DTPA-Derivative Chelator: Comparative Biodistribution and Imaging Studies of 111In-Labeled B3 Monoclonal Antibody in Athyrnic Mice Bearing Human Epidermoid Carcinoma Xenografts," Nucl. Med. Biol. 20(8):955-962.

Camera, L. et al. (Jul. 1994). "Comparative Biodistribution of Indium- and Yttrium-Labeled B3 Monoclonal Antibody Conjugated to Either 2-(p-SCN-Bz)-6-Methyl-DTPA (1B4M-DTPA) or 2-(p-SCN-Bz)-1,4,7,10-Tetraazacyclododecane Tetraacetic Acid (2B-DOTA)," European Journal of Nuclear Medicine 21(7):640-646.

Charlton, K.A. (2003). "Expression and Isolation of Recombinant Antibody Fragments in E. coli," Chapter 14 in Methods in Molecular Biology, LO, B.K.C. (ed.), Humana Press, Totowa, NJ, 248:245-254.

Chen, X. et al. (2004, e-published on Dec. 30, 2003). "MicroPET and Autoradiographic Imaging of Breast Cancer αv-Integrin Expression Using 18F- and 64Cu-Labeled RGD Peptide," Bioconjugate Chem. 15(1):41-49.

Chen, Y. et al. (1999). "Selection and Analysis of an Optimized Anti-VEGF Antibody: Crystal Structure of an Affinity-Matured Fab in Complex With Antigen," J. Mol. Bio. 293:865-881.

Chothia, C. et al. (1987). "Canonical Structures for the Hypervariable Regions of Immunoglobulins," J. Mol. Biol. 196:901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Cunningham, B.C. et al. (Jun. 2, 1989). "High-Resolution Epitope Mapping of hGH-Receptor Interactions by Alanine-Scanning Mutagenesis," Science 244:1081-1085.

Dail, M. et al. (Dec. 3-6, 2016). "Distinct Patterns of PD-L1 and PD-L2 Expression by Tumor and Non-Tumor Cells in Patients with MM, MDS, and AML," 58th American Society of Hematology Annual Meeting, 1 page.

Denardo, G.L. et al. (Oct. 1998). "Comparison of 1,4, 7 ,10-Tetraazacyclododecane-N,N',N'',N'''-Tetraacetic Acid (DOTA)-Peptide-ChL6, A Novel Immunoconjugate with Catabolizable Linker, to 2-Iminothiolane-2[p-(Bromoacetamido)Benzyl]-DOTA-ChL6 in Breast Cancer Xenografts," Clin. Cancer Res. 4:2483-2490.

Flatman. S. et al. (2007, e-pub. Dec. 11, 2006). "Process Analytics for Purification of Monoclonal Antibodies," J. Chromatogr. B. 848:79-87.

Gerngross, T.U. (Nov. 2004). "Advances in the Production of Human Therapeutic Proteins in Yeasts and Filamentous Fungi," Nature Biotechnology 22(11):1409-1414.

Goding, J.W. (1983). Monoclonal Antibodies: Principles and Practice, pp. 56-103.

Graham, F.L. et al. (1977). "Characteristics of a Human Cell Line Transformed by DNA From Human Adenovirus Type 5," Journal General Virology 36(1):59-74.

Griffiths, A.D. et al. (1993), "Human Anti-Self Antibodies with High Specificity from Phage Display Libraries," EMBO J, 12(2):725-734.

Hao, G. et al. (Apr. 9, 2015, e-pub. Feb. 9, 2015). "Epitope Characterization of an Anti-PD-L1 Antibody Using Orthogonal Approaches," Journal of Molecular Recognition, 28(4):269-276.

Harlow, E. et al. (1988) Antibodies: A Laboratory Manual, Cold Spring Harbor Laboratory pp. 53-137.

Hnatowich, D.J. et al. (1983). "The Preparation of DTPA-Coupled Antibodies Radiolabeled With Metallic Radionuclides: An Improved Method," Journal of Immunological Methods 65:147-157.

Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.

Hoogenboom, ¬H.R. et al. (Sep. 1991). "By-Passing Immunisation: Human Antibodies from Synthetic Repertoires of Germline VH Gene Segments Rearranged in vitro," Journal of Molecular Biology 227(2):381-388.

International Preliminary Report on Patentability, dated Jun. 2, 2020, for PCT Application No. PCT/US2018/062999, filed Nov. 29, 2018, 8 pages.

International Search Report and Written Opinion of the International Searching Authority, dated Feb. 18, 2019, fort PCT Application No. PCT/US2018/062999, filed Nov. 29, 2018, 16 pages.

Izard, M.E. et al. (1992). "An Improved Method for Labeling Monoclonal Antibodies With Samarium-153: Use of the Bifunctional Chelate 2-(p-isothlocyanatobenzyl)-6-Methyldiethylenetriaminepentaacetic Acid," Bioconjugate Chem. 3(4):346-350.

Kabat, E.A. et al. (1991). Sequences of Proteins of immunological interest, 5th Ed. Public Health Service, National Institutes of Health, Bethesda MD., Table of Contents, 21 pages.

Kindt, T.J. et al. (2007), "Antigens and Antibodies," in Chapter 4 of Kuby Immunology, 6th ed., W.H. Freeman and Co., N.Y. pp. 91, 14 pages.

Kobayashi, H. et al. (1999, e-pub. Dec. 10, 1998). "Evaluation of the In Vivo Biodistribution of Indium-111 and Yttrium-88 Labeled Dendrimer-1B4M-DTPA and Its Conjugation With Anti-Tac Monoclonal Antibody," Bioconjugate Chem, 10(1):103-111.

Kobayashi, H. et al. "Evaluation of the In Vivo Biodistribution of Yttrium-Labeled Isomers of CHX-DTPA-Conjugated Monoclonal Antibodies," J. Nucl. Med. 39:829-836.

Kohler, G. et al. (Aug. 7, 1975) "Continuous Cultures of Fused Cells Secreting Antibody of Predefined Specificity," Nature 256:495-497.

Kozbor, D. (Dec. 1984). "A Human Hybrid Myeloma for Production of Human Monoclonal Antibodies," J. Immunol. 133(6):3001-3005.

Kukis, D.L. et al. (Dec. 1998). "Optimized Conditions for Chelation of Yttrium-90-Dota Immunoconjugates," The Journal of Nuclear Medicine 39(12):2105-2110.

Lee, F.-T. et al. (Jun. 1, 2001). "Specific Localization, Gamma Camera Imaging, and Intracellular Trafficking of Radiolabeiled Chimeric Anti-G(d3) Ganglioside Monoclonal Antibody KM871 in SK-MEL-28 Melanoma Xenografts," Cancer Research 61(11):4474-4482.

Lee, J.Y. et al. (Oct. 31, 2016). "Structural Basis of Checkpoint Blockade by Monoclonal Antibodies in Cancer Immunotherapy," Nature Communication, 7:13354, 10 pages.

Lewis, M.R. et al. (Jan.-Feb. 1998, e-pub. Jan. 12, 1998). "Maleimidocysteineamido-DOTA Derivatives: New Reagents for Radiometal Chelate Conjugation to Antibody Sulfhydryl Groups Undergo pH-Dependent Cleavage reactions," Bioconj, Chem. 9(1):72-86.

Li, H. et al. (Feb. 2006, e-published on Jan. 22, 2006). "Optimization of Humanized IgGs in Glycoengineered Pichia pastoris," Nature Biotechnology 24(2):210-215.

Mardirossian, G. et al. (1993). "The Stability in Liver Homogenates of Indium-111 and Yttrium-90 Attached to Antibody via Two Popular Chelators," Nucl. Med. Biol. 20(1):65-74.

Marks, J.D. et al. (1991). "By-Passing Immunization. Human Antibodies From V-Gene Libraries Displayed on Phage," J. Mol. Biol. 222:581-597.

(56) References Cited

OTHER PUBLICATIONS

Marks, J.D. et al. (Jul. 1992). "By-Passing Immunization: Building High Affinity Human Antibodies by Chain Shuffling," Bio/Technoiogy 10: 779-783.
Mather, J.P. et al. (1980). "Establishment and Characterization of Two Distinct Mouse Testicular Epithelial Cell Lines," Biology of Reproduction 23:243-252.
Mather, J.P. et al. (1982) "Culture of Testicular Cells in Hormone-Supplemented Serum-Free Medium," Annals New York Academy of Sciences pp. 44-68.
McCafferty, J. et al. (Dec. 6, 1990). "Phage Antibodies: Filamentous Phage Displaying Antibody Variable Domains." Nature 348:552-554.
Meares, C.F. et al. (1990). "Macrocyclic Chelates of Radiometals for Diagnosis and Therapy," Br. J. Cancer 62 (Suppl. X):21-26.
Meares, C.F. et al. (1964). "Conjugation of Antibodies With Bifunctional Chelating Agents: Isothiocyanate and Bromoacetamide Reagents, Methods of Analysis, and Subsequent Addition of Metal Ions," Analytical Biochemistry 142:68-78.
Miederer, M. et al. (Jan. 2004). "Pharmacokinetics, Dosimetry, and Toxicity of the Targetable Atomic Generator, 225Ac-HuM195, In Nonhuman Primates," The Journal of Nuclear Medicine 45(1):129-137.
Miraglia, S. (1999). "Homogeneous Cell- and Bead-Based Assays for High Throughput Screening Using Fluorometric Microvolume Assay Technology," J. of Biomolecular Screening 4(4):193-204.
Mirzadeh, S. et al. (1990). "Radiometal Labeling of Immunoproteins: Covalent Linkage of 2-(4-Isothiocyanatobenzyl) Diethylenetriaminepentaacetic Acid Ligands to Immunoglobulin," Bioconjugate Chem. 1(1):59-65.
Mitchell, P. et al. (Jul. 2003). "Targeting Primary Human Ph+ B-cell Precursor Leukemia-engrafted SCID Mice Using Radiolabeled Anti-CD19 Monoclonal Antibodies," The Journal of Nuclear Medicine 44(7):1105-1112.
Morris, G.E. (1996). Epitope Mapping Protocols in Methods in Molecular Biology, vol. 66 (Humana Press, Totowa, New Jersey), 12 pages.
Mullis, K.B. et al. (1994). PCR: The Polymerase Chain Reaction, Mullis et al. eds., Birkauswer Press, Boston, 5 pages.
Munson, P.J. et al. (1980). "LIGAND: A Versatile Computerize Approach for Characterization of Ligand-Binding Systems," Anal. Biochem. 107:220-239.
Nikula, T.K. et al. (1995). "A Rapid, Single Vessel Method for Preparation of Clinical Grade Ligand Conjugated monoclonal Antibodies," Nucl. Med. Biol. 22(3):387-390.
Nikula, T.K. et al. (Jan. 1999). "Alpha-Emitting Bismuth Cyclohexylbenzyl DTPA Constructs of Recombinant Humanized Anti-CD33 Antibodies: Pharmacokinetics, Bioactivity, Toxicity and Chemistry," The Journal of Nuclear Medicine 40(1):166-176.
O'Sullivan, M.J. et al. (1981). "Methods for the Preparation of Enzyme-antibody Conjugates for Use in Enzyme Immunoassay," In Methods in Enzymology 73:147-166.
Plückthun, A. (1992). "Mono- and Bivalent Antibody Fragments Producted in *Escherichia coli*: Engineering, Folding and Antigen Binding," Immunol. Revs. 130:151-188.
Portolano, S. et al. (Feb. 1, 1993). "Lack of Promiscuity in Autoantigen-Specific H and L Chain Combinations as Revealed by Human H and L Chain 'Roulette'," The Journal of Immunology 150(3):880-887.
Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.
Roselli, M. et al. (1999). "In Vivo Comparison of CHX-DTPA Ligand Isomers in Athymic Mice Bearing Carcinoma Xenografts," Cancer Biotherapy & Radiopharmaceuticals 14(3):209-220.
Ruegg, C.L. et al. (Jul. 15, 1990). "Improved In Vivo Stability and Tumor Targeting of Bismuth-Labeled Antibody," Cancer Research 50:4221-4226.

Sambrook, J, et al. (1989). Molecular Cloning: A Laboratory Manual, 2nd ed., Cold Spring Harbor Laboratory, Cold Spring Harbor, NY, Table of Contents, v-xxxii, 29 pages.
Santini, F.C. et al. (Sep. 2017, e-pub. Jul. 27, 2017). "Atezolizumab for the Treatment of Non-Small Cell Lung Cancer," Expert Review of Clinical Pharmacology, 10(9):935-945, 28 pages.
Schats, K. et al. (Jun. 2, 2019). "Epitope Mapping of PD-L1 Primary Antibodies (28-8, SP142, SP263, E1L3N)," HistoGeneX, 3 pages.
Schats, K. et al. (May 30, 2017). "Epitope Mapping of PD-L1 Primary Antibodies (28-8, SP142, SP263, E1L3N)," Journal of Clinical Oncology 35(15):1-5, Abstract Only.
Singh, R. et al. (May 15, 2002), "Labeling of Antibodies by In Situ Modification of Thiol Groups Generated From Selenoi-Catalyzed Reduction of Native Disulfide Bonds," Analytical Biochemistry 304(2):147-156.
Singleton, P. et al. (1994), Dictionary of Microbiology and Molecular Biology, 2nd ed. New York, New York, 8 pages.
Skerra, A. (1993) "Bacterial Expression of Immunoglobulin Fragments," Current Opinion in Immunology 5:256-262.
Swartzman, E.E. (1999). "A Homogeneous and Multiplexed Immunoassay for High-Throughput Screening Using Fluorometric Microvolume Assay Technology," Anal. Biochem. 271:143-151.
Tan, S, et al. (May 9, 2018), "Distinct PD-L1 Binding Characteristics of Therapeutic Monoclonal Antibody Durvalumab," Protein & Cell 9(1):135-139.
U.S. Appl. No. 14/303,153, filed Jun. 12, 2014, for Irving et al. (Copy not submitted herewith pursuant to the waiver of 37 C.F.R. § 1.98(a)(2)(iii) issued by the Office on Sep. 21, 2004).
U.S. Appl. No. 14/455,656, filed Aug. 8, 2014, for Irving et al. (Copy not submitted herewith pursuant to the waiver of 37 C.F.R. § 1.98(a)(2)(iii) issued by the Office on Sep. 21, 2004).
U.S. Appl. No. 14/536,901, filed May 23, 2012, for Irving et al. (Copy not submitted herewith pursuant to the waiver of 37 C.F.R. § 1.98(a)(2)(iii) issued by the Office on Sep. 21, 2004).
U.S. Appl. No. 14/610,593, filed Jan. 30, 2015, for Irving et al. (Copy not submitted herewith pursuant to the waiver of 37 C.F.R. § 1.98(a)(2)(iii) issued by the Office on Sep. 21, 2004).
U.S. Appl. No. 14/789,678, filed May 23, 2012, for Irving et al. (Copy not submitted herewith pursuant to the waiver of 37 C.F.R. § 1.98(a)(2)(iii) issued by the Office on Sep. 21, 2004).
U.S. Appl. No. 14/825,779, filed May 23, 2012, for Irving et al. (Copy not submitted herewith pursuant to the waiver of 37 C.F.R. § 1.98(a)(2)(iii) issued by the Office on Sep. 21, 2004).
U.S. Appl. No. 15/043,846, filed Feb. 15, 2016, for Irving et al. (Copy not submitted herewith pursuant to the waiver of 37 C.F.R. § 1.98(a)(2)(iii) issued by the Office on Sep. 21, 2004).
U.S. Appl. No. 15/075,616, filed Mar. 21, 2016, for Irving et al. (Copy not submitted herewith pursuant to the waiver of 37 C.F.R. § 1.98(a)(2)(iii) issued by the Office on Sep. 21, 2004).
U.S. Appl. No. 15/881,612, filed Jan. 26, 2018, for Irving et al. (Copy not submitted herewith pursuant to the waiver of 37 C.F.R. § 1.98(a)(2)(iii) issued by the Office on Sep. 21, 2004).
U.S. Appl. No. 16/854,707, filed Apr. 21, 2020, for Irving et al. (Copy not submitted herewith pursuant to the waiver of 37 C.F.R. § 1.98(a)(2)(iii) issued by the Office on Sep. 21, 2004).
Urlaub, G. et al. (Jul. 1980). "Isolation of Chinese hamster cell mutants deficient in dihydrofolate reductase activity," Proc. Natl. Acad. Sci. USA 77(7):4216-4220.
Verel, I. et al. (Oct. 2003). "Quantitative 89Zr Immuno-PET for in Vivo Scouting of 90Y-Labeled Monoclonal Antibodies in Xenograft-bearing Nude Mice," The Journal of Nuclear Medicine 44(10):1663-1670.
Vermes, I. (Jul. 17, 1995). "A Novel Assay for Apoptosis. Flow Cytometric Detection of Phosphatidylserine Expression on Early Apoptotic Cells Using Fluorescein Labelled Annexin V," J. Immunol. Methods 184(1):39-51.
Waterhouse, P. et al. (1993). "Combinatorial Infection and In Vivo Recombination: A Strategy for Making Large Phage Antibody Repertoires," Nucleic Acids Research 21(9):2265-2266.
Winter, G. et al. (1994). "Making Antibodies by Phage Display Technology," Ann. Rev. Immunol. 12:433-455.

(56) References Cited

OTHER PUBLICATIONS

Wu, A.M. et al. (Sep. 2005, e-pub. Sep. 7, 2005). "Arming Antibodies: Prospects and Challenges for Immunoconjugates," Nature Biotechnology 23(9):1137-1146.

Yadav, M. et al. (Dec. 3-6, 2016). "TIGIT, CD226, and PD-L1/PD-1 Are Highly Expressed by Marrow-Infiltrating T Cells in Patients With Multiple Myeloma," 58th American Society of Hematology Annual Meeting, 1 page.

Yazaki, P.J. et al. (2003). "Expression of Recombinant Antibodies in Mammalian Cell Lines," Methods in Molecular Biology, vol. 248 B.K.C. Lo, ed., Humana Press, Totowa, N.J. pp. 255-268.

Zheng, T.S. (Nov. 1998), "Caspase-3 Controls Both Cytoplasmic and Nuclear Events Associated With Fas-Mediated Apoptosis in vivo." Proc. Natl. Acad. Sci. USA 95:13618-13623.

\* cited by examiner

FIG. 1A

Heavy chain: Mouse antibody aligned to mouse germlines

```
Kabat number    1  2  3  4  5  6  7  8  9  10 11 12 13 14 15 16 17 18 19 20 21 22 23 24 25 26 27 28 29 30 31 32 33 34 35 36 37 38 39 40 41 42 43 44
                Q  V  Q  L  Q  Q  S  G  P  E  L  V  K  P  G  A  S  V  K  I  S  C  K  A  S  G  Y  A  F  S  S  S  W  M  N  .  W  V  K  Q  R  P  G  K  G
IGHV1-82*01     Q  V  Q  L  Q  Q  S  G  P  E  L  V  K  P  G  A  S  V  K  I  S  C  K  A  S  G  Y  A  F  S  S  S  W  M  N  .  W  V  K  Q  R  P  G  K  G
                                                                                                        [CDR H1          ]

Kabat number    45 46 47 48 49 50 51 52 a  53 54 55 56 57 58 59 60 61 62 63 64 65 66 67 68 69 70 71 72 73 74 75 76 77 78 79 80 81 82 a  b  c  83 84
                L  E  W  I  G  R  I  Y  P  .  G  D  G  D  T  N  Y  N  G  K  F  K  G  K  A  T  L  T  A  D  K  S  S  S  T  A  Y  M  Q  L  S  S  L  T  S
IGHV1-82*01     L  E  W  I  G  R  I  Y  P  .  G  D  G  D  T  Y  N  G  K  F  K  G  K  A  T  L  T  A  D  K  S  S  S  T  A  Y  M  Q  L  S  S  L  T  S
                                  [CDR H2                                  ]

Kabat number    85 86 87 88 89 90 91 92 93 94 95 96 97 98 99        100 a  101 102 103 104 105 106 107 108 109 110 111 112 113
                E  D  S  A  V  Y  F  C  A  R  .  .  N  P  G  G  Y  .  .  .  .  .  Y  F  D  Y  W  G  Q  G  T  T  L  T  V  S  S      SEQ ID NO:21
IGHV1-82*01     E  D  S  A  V  Y  F  C  .  .  .  .  .  .  .  .  .  .  .  .  .  .  Y  F  D  Y  W  G  Q  G  T  T  L  T  V  S  S      SEQ ID NO:7
                                       [CDR H3                                    ]
```

FIG. 1B

Light chain, Kappa: Mouse antibody aligned to mouse germlines

```
Kabat number    1  2  3  4  5  6  7  8  9 10 11 12 13 14 15 16 17 18 19 20 21 22 23 24 25 26 27    28 29 30 31 32 33 34 35 36
IGKV10-96*02    D  I  Q  M  T  Q  T  T  S  S  L  S  A  S  L  G  D  R  V  T  I  S  C  R  A  S  Q  .  .  .  .  D  I  S  N  Y  L  N  W  Y
                D  I  Q  M  T  Q  T  T  S  S  L  S  A  S  L  G  D  R  V  T  I  N  C  R  A  S  Q  .  .  .  .  D  I  T  Y  L  N  W  Y
                                                                                      CDR L1

Kabat number   37 38 39 40 41 42 43 44 45 46 47 48 49 50 51 52 53 54    55 56 57 58 59 60 61 62 63 64 65 66 67 68 69 70 71
IGKV10-96*02    Q  Q  K  P  D  G  T  V  K  L  L  I  Y  Y  T  S  R  L  .  .  H  S  G  V  P  S  R  F  S  G  S  G  S  G  T  D  Y
                Q  Q  K  P  D  G  T  V  K  L  L  I  Y  Y  T  S  R  L  .  .  H  S  G  V  P  S  R  F  S  G  S  G  S  G  T  D  Y
                                              CDR L2

Kabat number   72 73 74 75 76 77 78 79 80 81 82 83 84 85 86 87 88 89 90 91 92 93 94 95 a    96 97 98 99 100 101 102 103 104 105 106 107
IGKV10-96*02    S  L  T  I  S  N  L  E  Q  E  D  I  A  T  Y  F  C  Q  Q  G  S  T  L  P  .  .  W  T  F  G  G  G  T  K  L  L  E  I  K    SEQ ID NO:22
                S  L  T  I  S  N  L  E  Q  E  D  I  A  T  Y  F  C  Q  Q  S  S  L  P  .  .  .  W  T  F  G  G  G  T  K  L  E  I  K      SEQ ID NO:8
                                                                      CDR L3
```

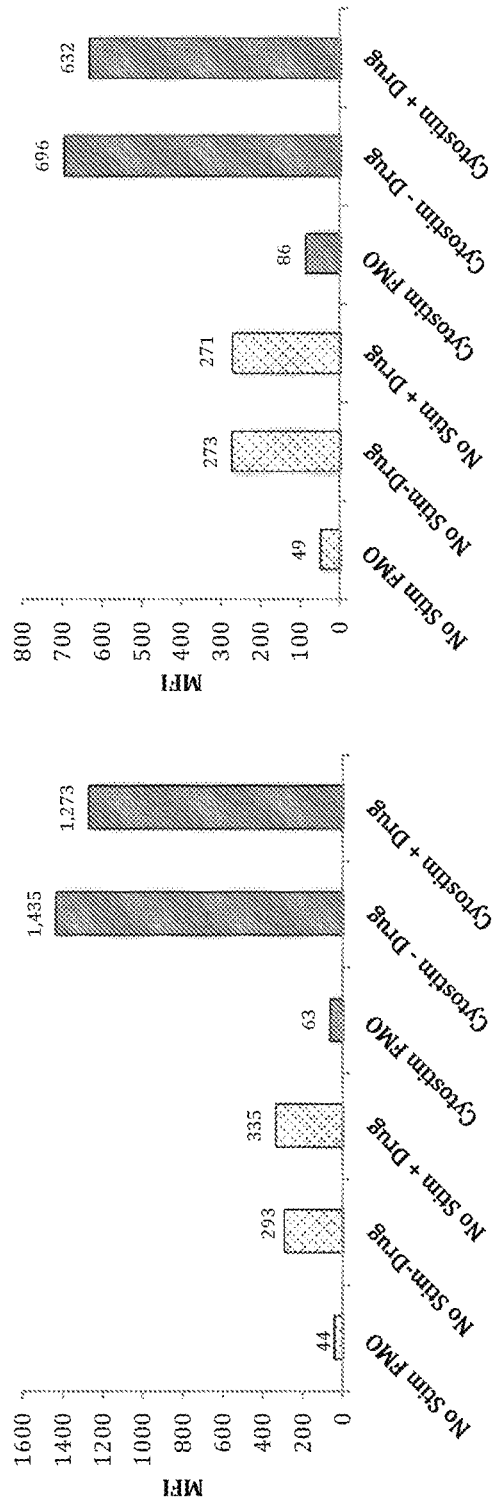
FIG. 14A
FIG. 14B
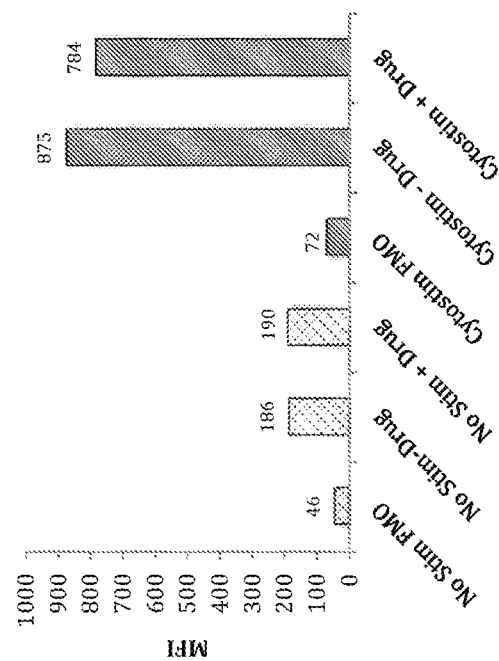
FIG. 14C

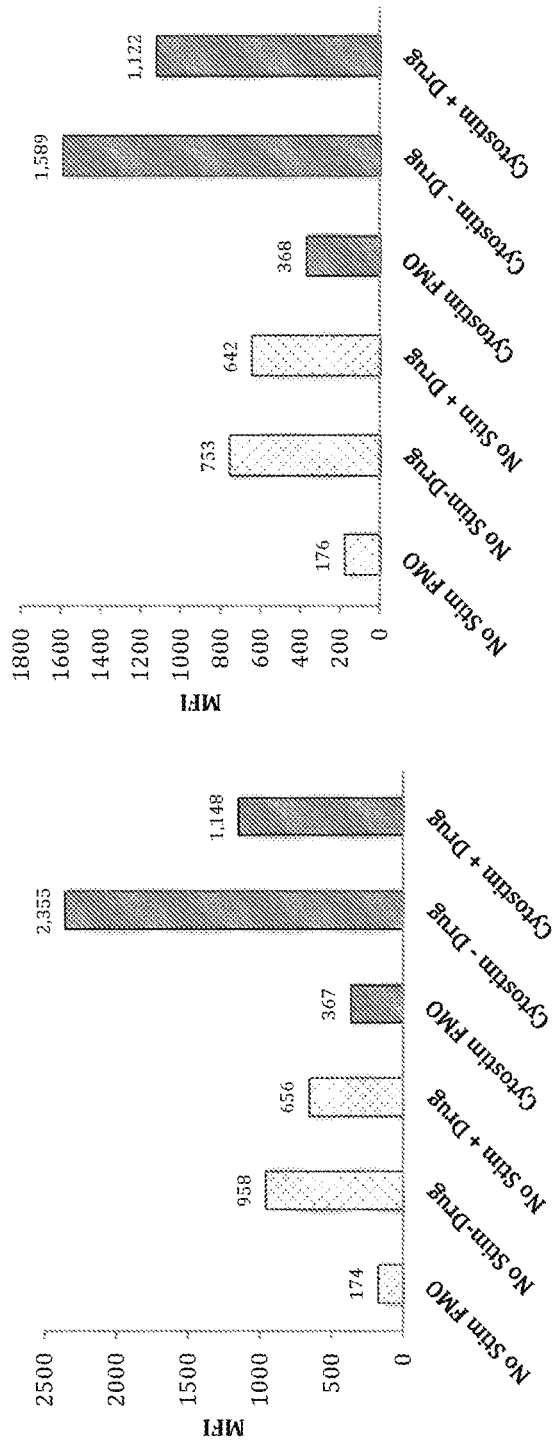
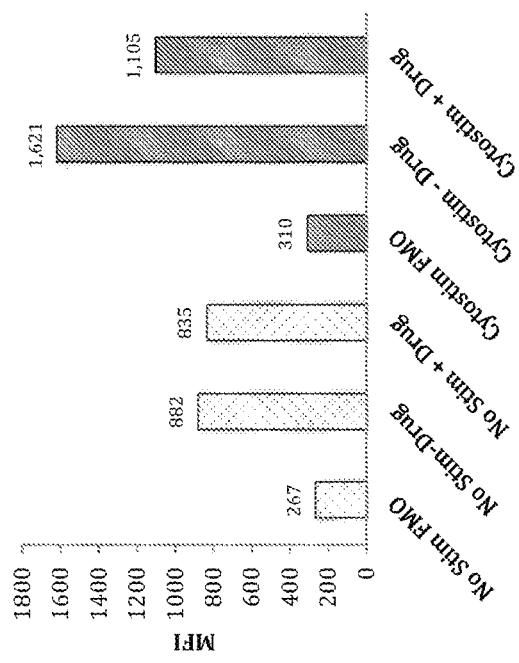
FIG. 16A
FIG. 16B
FIG. 16C

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
```

<223> OTHER INFORMATION: Synthetic Construct

<400> SEQUENCE: 1

Thr Ser Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Arg Ile Tyr Pro Arg Asp Gly Asp Thr Tyr Tyr Asn Gly Lys Phe Lys
1               5                   10                  15

Asp

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Asn Pro Gly Gly Tyr Tyr Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Arg Ala Ser Gln Asp Ile His Thr Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Tyr Thr Ser Arg Leu His Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gln Gln Val Ser Ser Leu Pro Pro Trp Thr
1               5                   10

<210> SEQ ID NO 7
<211> LENGTH: 118
<212> TYPE: PRT
<213> ORGANISM: Artificial Sequence

```
<220> FEATURE:
<223> OTHER INFORMATION: Synthetic Construct

<400> SEQUENCE: 7

Gln Val Gln Leu Gln Gln Ser Gly Pro Glu Leu Val Asn Pro Gly Ala
1               5                   10                  15

Ser Val Lys Ile Ser Cys Lys Ala Ser Gly Tyr Ala Phe Ser Thr Ser
                20                  25                  30

Trp Met Asn Trp Val Lys Gln Arg Pro Gly Lys Gly Leu Glu Trp Ile
            35                  40                  45

Gly Arg Ile Tyr Pro Arg Asp Gly Asp Thr Tyr Tyr Asn Gly Lys Phe
        50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Thr Lys Asn Pro Gly Gly Tyr Tyr Phe Asp Tyr Trp Gly Gln Gly Thr
                100                 105                 110

Thr Leu Thr Val Ser Ser
            115

<210> SEQ ID NO 8
<211> LENGTH: 108
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile His Thr Tyr
                20                  25                  30

Leu Asn Trp Tyr Gln Gln Lys Pro Asp Gly Thr Val Lys Leu Leu Ile
            35                  40                  45

Phe Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Val Ser Ser Leu Pro Pro
                85                  90                  95

Trp Thr Phe Gly Gly Gly Thr Lys Val Glu Ile Lys
                100                 105

<210> SEQ ID NO 9
<211> LENGTH: 447
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Gln Gln Ser Gly Pro Glu Leu Val Asn Pro Gly Ala
1               5                   10                  15

Ser Val Lys Ile Ser Cys Lys Ala Ser Gly Tyr Ala Phe Ser Thr Ser
                20                  25                  30

Trp Met Asn Trp Val Lys Gln Arg Pro Gly Lys Gly Leu Glu Trp Ile
            35                  40                  45
```

```
Gly Arg Ile Tyr Pro Arg Asp Gly Asp Thr Tyr Tyr Asn Gly Lys Phe
         50                  55                  60

Lys Asp Lys Ala Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Phe Cys
                 85                  90                  95

Thr Lys Asn Pro Gly Gly Tyr Tyr Phe Asp Tyr Trp Gly Gln Gly Thr
                100                 105                 110

Thr Leu Thr Val Ser Ser Ala Ser Thr Lys Gly Pro Ser Val Tyr Pro
            115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445

<210> SEQ ID NO 10
<211> LENGTH: 215
<212> TYPE: PRT
```

<213> ORGANISM: Artificial Sequence
<220> FEATURE:
<223> OTHER INFORMATION: Synthetic Construct

<400> SEQUENCE: 10

```
Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile His Thr Tyr
            20                  25                  30

Leu Asn Trp Tyr Gln Gln Lys Pro Asp Gly Thr Val Lys Leu Leu Ile
        35                  40                  45

Phe Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65              70                  75                  80

Glu Asp Ile Ala Thr Tyr Phe Cys Gln Gln Val Ser Ser Leu Pro Pro
                85                  90                  95

Trp Thr Phe Gly Gly Gly Thr Lys Val Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

```
Gly Phe Thr Phe Ser Asp Ser Trp Ile His
1               5                   10
```

<210> SEQ ID NO 12
<211> LENGTH: 18
<212> TYPE: PRT
<213> ORGANISM: Artificial Sequence
<220> FEATURE:
<223> OTHER INFORMATION: Synthetic Construct

<400> SEQUENCE: 12

```
Ala Trp Ile Ser Pro Tyr Gly Gly Ser Thr Tyr Tyr Ala Asp Ser Val
1               5                   10                  15

Lys Gly
```

<210> SEQ ID NO 13
<211> LENGTH: 9

<212> TYPE: PRT
<213> ORGANISM: Artificial Sequence
<220> FEATURE:
<223> OTHER INFORMATION: Synthetic Construct

<400> SEQUENCE: 13

Arg His Trp Pro Gly Gly Phe Asp Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Arg Ala Ser Gln Asp Val Ser Thr Ala Val Ala
1               5                  10

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Ser Ala Ser Phe Leu Tyr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Gln Gln Tyr Leu Tyr His Pro Ala Thr
1               5

<210> SEQ ID NO 17
<211> LENGTH: 118
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

```
Leu Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 19
<211> LENGTH: 447
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
            180                 185                 190
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 20
<211> LENGTH: 214
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
```

```
                100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 113
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Phe Asp Tyr Trp Gly Gln Gly Thr Thr Leu Thr Val Ser
            100                 105                 110

Ser

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
```

```
                65                  70                  75                  80
Glu Asp Ile Ala Thr Tyr Phe Cys Gln Gln Gly Ser Thr Leu Pro Trp
                        85                  90                  95
Thr Phe Gly Gly Gly Thr Lys Leu Glu Ile Lys
                100                 105
```

ANTI-PD-L1 ANTIBODIES AND METHODS OF USING THE SAME FOR DETECTION OF PD-L1

RELATED APPLICATIONS

This application is a continuation of International Application No. PCT/US2018/062999, filed on Nov. 29, 2018, which claims priority benefit to U.S. Patent Application No. 62/593,125, filed Nov. 30, 2017, the disclosure of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392040101SEQLIST.TXT, date recorded: May 26, 2020, size: 20 KB).

FIELD OF THE INVENTION

The present invention relates to anti-PD-L1 antibodies and methods of using the same for detection of PD-L1.

BACKGROUND OF THE INVENTION

It has been discovered that T cell dysfunction or anergy occurs concurrently with an induced and sustained expression of the inhibitory receptor, programmed death 1 polypeptide (PD-1). As a result, therapeutics targeting PD-1 and other molecules which signal through interactions with PD-1, such as programmed death ligand 1 (PD-L1), are an area of intense interest. The inhibition of PD-L1 signaling has been demonstrated as a means to enhance T cell immunity for the treatment of cancer (e.g., tumor immunity). Therapies which use anti-PD-1 or anti-PD-L1 antibodies have been developed and used for treating different types of cancers. See, e.g., U.S. Pat. No. 8,217,149.

There is a need in the art to detect PD-L1 in biological samples from subjects who have been treated with a therapeutic anti-PD-L1 antibody. The invention provides anti-PD-L1 antibodies that specifically detect PD-L1, without competing for binding to PD-L1 with therapeutic anti-PD-L1 antibodies. These antibodies are useful, for example, in monitoring cancer treatment in subjects who have been treated with a therapeutic anti-PD-L1 antibody.

SUMMARY OF THE INVENTION

In one aspect, the present invention provides an isolated anti-PD-L1 antibody, or an antigen-binding fragment thereof, wherein the antibody comprises:
(a) a heavy chain variable region comprising:
  (i) HVR-H1 comprising the amino acid sequence TSWMN (SEQ ID NO: 1);
  (ii) HVR-H2 comprising the amino acid sequence RIYPRDGDTYYNGKFKD (SEQ ID NO:2); and
  (iii) HVR-H3 comprising the amino acid sequence NPGGYYFDY (SEQ ID NO:3); and
(b) a light chain variable region comprising:
  (i) HVR-L1 comprising the amino acid sequence RASQDIHTYLN (SEQ ID NO:4);
  (ii) HVR-L2 comprising the amino acid sequence YTSRLHS (SEQ ID NO:5); and
  (iii) HVR-L3 comprising the amino acid sequence QQVSSLPPWT (SEQ ID NO:6).

In some embodiments, the antibody or antigen-binding fragment comprises a heavy chain variable region comprising the amino acid sequence of SEQ ID NO:7, and a light chain variable region comprising the amino acid sequence of SEQ ID NO:8. In some embodiments, the antibody comprises a heavy chain comprising the amino acid sequence of SEQ ID NO:9, and a light chain comprising the amino acid sequence of SEQ ID NO: 10.

In some of any of the embodiments herein, the antibody or antigen-binding fragment does not compete with a reference antibody for binding to human PD-L1, wherein the reference antibody comprises:
(a) a heavy chain variable region comprising:
  (i) HVR-H1 comprising the amino acid sequence GFTFSDSWIH (SEQ ID NO: 11);
  (ii) HVR-H2 comprising the amino acid sequence AWISPYGGSTYYADSVKG (SEQ ID NO: 12); and
  (iii) HVR-H3 comprising the amino acid sequence RHWPGGFDY (SEQ ID NO: 13); and
(b) a light chain variable region comprising:
  (i) HVR-L1 comprising the amino acid sequence RASQDVSTAVA (SEQ ID NO: 14);
  (ii) HVR-L2 comprising the amino acid sequence SASFLYS (SEQ ID NO: 15); and
  (iii) HVR-L3 comprising the amino acid sequence QQYLYHPAT (SEQ ID NO: 16).

In some embodiments, the reference antibody comprises a heavy chain variable region comprising the amino acid sequence of SEQ ID NO: 17, and a light chain variable region comprising the amino acid sequence of SEQ ID NO: 18. In some embodiments, the reference antibody comprises a heavy chain comprising the amino acid sequence of SEQ ID NO:19, and a light chain comprising the amino acid sequence of SEQ ID NO:20.

In some of any embodiments herein, the antibody or antigen-binding fragment is linked to a moiety. In some embodiments, the moiety is a detectable moiety. In some embodiments, the detectable moiety is biotin, streptavidin, a luminescent agent, an enzyme, a fluorophore, a dye, a radiolabel, a chromophore, a metal ion, a gold particle, a silver particle, a magnetic particle, a polypeptide, or an oligonucleotide. In some embodiments, the detectable moiety is a fluorophore. In some embodiments, the fluorophore is R-phycoerythrin (PE), PE-Cy7, Alexa Fluor 488, fluorescein isothiocyanate (FITC), peridinin chlorophyll protein complex (PerCP), BV421, BV510, APC-H7, Alexa Fluor 647 or allophycocyanin (APC).

In another aspect, the present invention provides an isolated nucleic acid encoding an antibody or antigen-binding fragment described herein.

In another aspect, the present invention provides a vector comprising a nucleic acid as described herein. In some embodiments, the vector is an expression vector.

In another aspect, the present invention provides a host cell comprising a nucleic acid as described herein.

In another aspect, the present invention provides a method of producing an anti-PD-L1 antibody or antigen-binding fragment thereof described herein, comprising culturing a host cell described herein under a condition suitable for production of the anti-PD-L1 antibody or antigen-binding fragment thereof. In some embodiments, the method further comprises recovering the anti-PD-L1 antibody, or antigen-binding fragment thereof produced by the host cell.

In another aspect, the present invention provides a method for detecting PD-L1 in a biological sample obtained from a subject, the method comprising: (a) contacting the biological sample with an antibody or antigen-binding fragment described herein; and (b) detecting binding of the antibody or antigen-binding fragment to PD-L1 in the biological sample, thereby detecting PD-L1 in the biological sample. In some embodiments, the antibody or antigen-binding fragment is detected using flow cytometry. In some of any of the embodiments herein, the biological sample is a blood sample. In some of any of the embodiments herein, the biological sample is a bone marrow sample. In some of any of the embodiments herein, the biological sample is a cell or tissue. In some embodiments, the cell or tissue is a cancerous cell or cancerous tissue. In some of any of the embodiments herein, the biological sample comprises live cells. In some of any of the embodiments herein, the subject has a cancer. In some embodiments, the cancer is selected from the group consisting of multiple myeloma, myelodysplastic syndrome, and acute myeloid leukemia. In some of any of the embodiments herein, the biological sample is obtained from a subject that has been administered a therapeutic anti-PD-L1 antibody or antigen-binding fragment thereof, wherein the therapeutic antibody or antigen-binding fragment thereof comprises:
  (a) a heavy chain variable region comprising:
    (i) HVR-H1 comprising the amino acid sequence GFTFSDSWIH (SEQ ID NO: 11);
    (ii) HVR-H2 comprising the amino acid sequence AWISPYGGSTYYADSVKG (SEQ ID NO: 12); and
    (iii) HVR-H3 comprising the amino acid sequence RHWPGGFDY (SEQ ID NO: 13); and
  (b) a light chain variable region comprising:
    (i) HVR-L1 comprising the amino acid sequence RASQDVSTAVA (SEQ ID NO: 14);
    (ii) HVR-L2 comprising the amino acid sequence SASFLYS (SEQ ID NO: 15); and
    (iii) HVR-L3 comprising the amino acid sequence QQYLYHPAT (SEQ ID NO: 16).

In some embodiments, the therapeutic antibody or antigen-binding fragment thereof comprises a heavy chain variable region comprising the amino acid sequence of SEQ ID NO: 17, and a light chain variable region comprising the amino acid sequence of SEQ ID NO: 18. In some embodiments, the therapeutic antibody or antigen-binding fragment thereof comprises a heavy chain comprising the amino acid sequence of SEQ ID NO: 19, and a light chain comprising the amino acid sequence of SEQ ID NO:20. In some of any of the embodiments herein, the subject is a human.

In another aspect, the present invention provides a method of monitoring cancer treatment in a subject, the method comprising: (a) contacting a first biological sample with an antibody or antigen-binding fragment described herein; (b) detecting binding of the antibody or antigen-binding fragment to PD-L1 in the first biological sample; (c) determining the amount of PD-L1 present in the first biological sample; (d) contacting a second biological sample with an antibody or antigen-binding fragment described herein, wherein the second biological sample is obtained after treatment with a therapeutic anti-PD-L1 antibody or antigen-binding fragment thereof; (e) detecting binding of the antibody or antigen-binding fragment to PD-L1 in the second biological sample; (f) determining the amount of PD-L1 present in the second biological sample; (g) comparing the amount of PD-L1 present in the first biological sample to the amount of PD-L1 present in the second biological sample. In some embodiments, an increase in the amount of PD-L1 present in the second biological sample compared to the first biological sample indicates that the patient is not responding to treatment with the therapeutic anti-PD-L1 antibody. In some embodiments, a decrease in the amount of PD-L1 present in the second biological sample compared to the first biological sample indicates that the patient is responding to treatment with the therapeutic anti-PD-L1 antibody. In some of any of the embodiments herein, the first biological sample is obtained from the subject prior to treatment with the therapeutic anti-PD-L1 antibody or antigen-binding fragment thereof. In some of any of the embodiments herein, the first biological sample is obtained from the subject after treatment with the therapeutic anti-PD-L1 antibody or antigen-binding fragment thereof. In some of any of the embodiments herein, the first and second biological samples are blood samples. In some of any of the embodiments herein, the first and second biological samples are bone marrow samples. In some of any of the embodiments herein, the first and second biological samples are cells or tissues. In some embodiments, the cells or tissues are cancerous cells or cancerous tissues. In some of any of the embodiments herein, the first and second biological samples comprise live cells. In some of any of the embodiments herein, the subject has a cancer selected from the group consisting of multiple mycloma, myclodysplastic syndrome, and acute mycloid leukemia. In some of any of the embodiments herein, the therapeutic antibody or antigen-binding fragment thereof comprises:
  (a) a heavy chain variable region comprising:
    (i) HVR-H1 comprising the amino acid sequence GFTFSDSWIH (SEQ ID NO: 11);
    (ii) HVR-H2 comprising the amino acid sequence AWISPYGGSTYYADSVKG (SEQ ID NO: 12); and
    (iii) HVR-H3 comprising the amino acid sequence RHWPGGFDY (SEQ ID NO: 13); and
  (b) a light chain variable region comprising:
    (i) HVR-L1 comprising the amino acid sequence RASQDVSTAVA (SEQ ID NO: 14);
    (ii) HVR-L2 comprising the amino acid sequence SASFLYS (SEQ ID NO: 15); and
    (iii) HVR-L3 comprising the amino acid sequence QQYLYHPAT (SEQ ID NO: 16).

In some embodiments, the therapeutic antibody or antigen-binding fragment thereof comprises a heavy chain variable region comprising the amino acid sequence of SEQ ID NO: 17, and a light chain variable region comprising the amino acid sequence of SEQ ID NO: 18. In some embodiments, the therapeutic antibody or antigen-binding fragment thereof comprises a heavy chain comprising the amino acid sequence of SEQ ID NO: 19, and a light chain comprising the amino acid sequence of SEQ ID NO:20. In some of any of the embodiments herein, the anti-PD-L1 antibody or antigen-binding fragment is detected using flow cytometry. In some of any of the embodiments herein, the subject is a human.

In another aspect, the present invention provides a composition comprising the antibody or antigen-binding fragment described herein.

In another aspect, the present invention provides a kit for detecting PD-L1 in a biological sample comprising an antibody or antigen-binding fragment described herein or a composition described herein.

BRIEF DESCRIPTION OF THE FIGURES

FIGS. 1A and 1B is a diagram of a sequence alignment between A) the heavy chain variable region of 14D3 anti-PD-L1 (SEQ ID NO:7), and B) the light chain variable region of 14D3 anti-PD-L1 (SEQ ID NO:8) against the closest matching mouse germline (SEQ ID NO:21 in FIG. 1A and SEQ ID NO:22 in FIG. 1B).

FIG. 14A-C is a graph showing the median fluorescent intensity (MFI) of A) CD4+ T cells, B) CD8+ T cells and C) CD19 B cells in both unstimulated and stimulated blood obtained from healthy donors and stained with anti-PD-L1 PE 14.D3 antibody in the absence of Atezolizumab (− Drug) or in the presence of Atezolizumab (+ Drug). FMO indicates fluorescence minus one negative gating control. Cytostim indicates CytoStim® stimulation agent. No Stim FMO: anti-PD-L1 PE 14.D3 antibody not present; No Stim − Drug: anti-PD-L1 PE 14.D3 antibody was present; No Stim+ Drug: anti-PD-L1 PE 14.D3 antibody and Atezolizumab were present; Cytostim FMO: anti-PD-L1 PE 14.D3 antibody not present; Cytostim−Drug: anti-PD-L1 PE 14.D3 antibody was present; and Cytostim+ Drug: anti-PD-L1 PE 14.D3 antibody and Atezolizumab were present.

FIG. 16A-C is a graph showing the median fluorescent intensity (MFI) of A) CD4+ T cells, B) CD8+ T cells and C) CD19 B cells in both unstimulated and stimulated healthy blood obtained from healthy donors and stained with anti-PD-L1 APC 29E.23 antibody in the absence of Atezolizumab (− Drug) or in the presence of Atezolizumab (+ Drug). D3 antibody in the absence of Atezolizumab (− Drug) or in the presence of Atezolizumab (+ Drug). FMO indicates fluorescence minus one negative gating control. Cytostim indicates CytoStim® stimulation agent. No Stim FMO: anti-PD-L1 APC 29E.23 antibody not present; No Stim − Drug: anti-PD-L1 APC 29E.23 antibody was present; No Stim+ Drug: anti-PD-L1 APC 29E.23 antibody and Atezolizumab were present; Cytostim FMO: anti-PD-L1 APC 29E.23 antibody not present; Cytostim−Drug: anti-PD-L1 APC 29E.23 antibody was present; and Cytostim+ Drug: anti-PD-L1 APC 29E.23 antibody and Atezolizumab were present.

DETAILED DESCRIPTION OF EMBODIMENTS OF THE INVENTION

I. Definitions

Figure 2A:
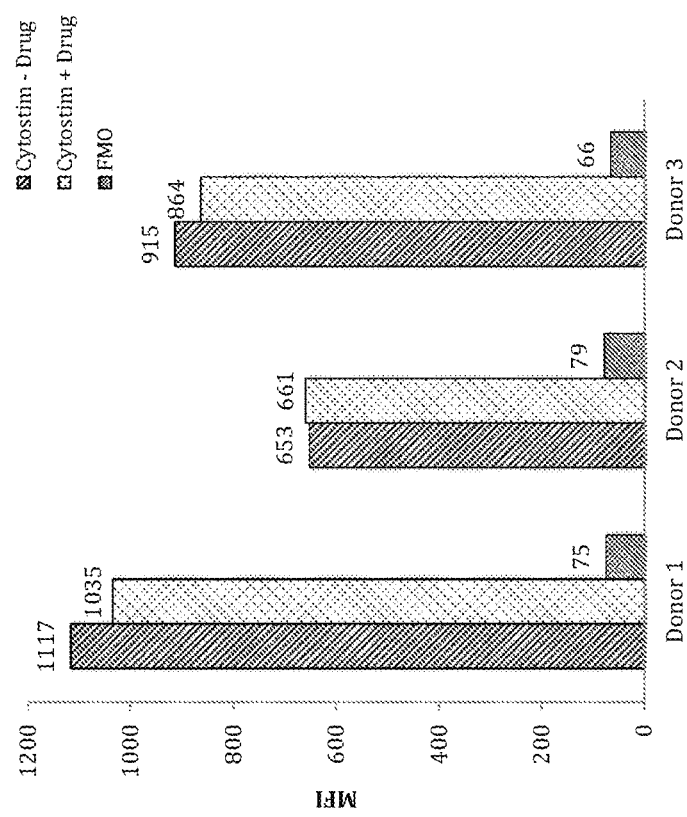
FIGS. 2A and 2B is a graph showing the median fluorescent intensity (MFI) of PD-L1+CD4+ T cells in blood obtained from healthy human donors and A) stained with anti-PD-L1 PE 29E.23 in the absence of Atezolizumab (− Drug) or in the presence of Atezolizumab (+ Drug) after stimulation with CytoStim® (Miltenyi Biotec); or B) stained with anti-PD-L1 PE 14.D3 in the absence of Atezolizumab (− Drug) or in the presence of Atezolizumab (+ Drug) after stimulation with CytoStim®. FMO indicates fluorescence minus one negative gating control.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds 1987, and periodic updates); *PCR: The Polymerase Chain Reaction*, (Mullis et al., ed., 1994); *A Practical Guide to Molecular Cloning* (Perbal Bernard V., 1988): *Phage Display: A Laboratory Manual* (Barbas et al., 2001).

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described herein.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called a, 8, y, y, and g, respectively.

The terms "anti-PD-L1 antibody", "anti-PD-L1", "PD-L1 antibody" or "an antibody that binds to PD-L1" refers to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an antibody that binds to PD-L1 has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$ M to $10^{-13}$ M, e.g., from $10^{-9}$ M to $10^{-13}$ M). In certain embodiments, an anti-PD-L1 antibody binds to an epitope of PD-L1 that is conserved among PD-L1 from different species. In certain embodiments, an anti-PD-L1 antibody binds to human PD-L1.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "chimeric" antibody refers to an antibody in which a portion of the heavy and/or light chain is derived from a particular source or species, while the remainder of the heavy and/or light chain is derived from a different source or species.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano ct al., *J. Immunol.* 150:880-887 (1993); Clarkson et al., *Nature* 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The "Fab" fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In certain embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In certain embodiments, the host cell is an "isolated" host cell, which refers to a host cell that has been separated from a component of its natural environment.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the singular form "a", "an", and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

It is understood that aspect and embodiments of the invention described herein include "comprising," "consisting," and "consisting essentially of" aspects and embodiments.

II. Anti-PD-L1 Antibodies for Detection of PD-L1

In one aspect, the invention provides anti-PD-L1 antibodies, which are useful, e.g., for detection and/or quantification of PD-L1 protein on the surface of cells in a biological sample. In some embodiments, the anti-PD-L1 antibody is monoclonal, chimeric or humanized. In some embodiments, the anti-PD-L1 is useful for detection and/or quantification of PD-L1 protein on the surface of live cells in a biological sample. In some embodiments, the biological sample is a peripheral blood sample or a cancer sample. In some embodiments, the biological sample is a bone marrow sample. In some embodiments, the biological sample comprises immune cells or tumor cells. In some embodiments, the sample is from a human subject. In some embodiments, the anti-PD-L1 antibody is used for detection and/or quantification of PD-L1 protein using flow cytometry. In some embodiments, the anti-PD-L1 antibody does not cross-compete for binding to PD-L1 with an anti-PD-L1 reference antibody. In some embodiments, the anti-PD-L1 reference antibody is atezolizumab. In some embodiments, the anti-PD-L1 antibody is useful for detecting the presence of PD-L1 in a subject who has received treatment with atezolizumab.

A. Exemplary Anti-PD-L1 Antibodies for Detection of PD-L1

Generally, antibodies of the disclosure immunospecifically bind PD-L1 (for example, human PD-L1). Antibodies of the disclosure are preferably monoclonal, and may be multispecific, human, humanized, mouse or chimeric, single chain antibodies, Fab fragments, F(ab') fragments, fragments produced by a Fab expression library, and PD-L1 binding fragments of any of the above. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the antibodies or antigen-binding fragments thereof as described herein are antigen-binding fragments. In certain embodiments, antigen-binding fragments include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. Preferably, the antibodies or antigen-binding fragments thereof are human, murine (e.g., mouse and rat), donkey, sheep, rabbit, goat, guinea pig, camelid, horse, or chicken.

Antibodies of the present disclosure may be described or specified in terms of the particular HVRs they comprise.

In certain embodiments, the invention provides anti-PD-L1 antibodies that comprise (a) a heavy chain variable region comprising HVR-H1 comprising the amino acid sequence TSWMN (SEQ ID NO: 1), HVR-H2 comprising the amino acid sequence RIYPRDGDTYYNGKFKD (SEQ ID NO:2), and HVR-H3 comprising the amino acid sequence NPGGYYFDY (SEQ ID NO:3); and (b) a light chain variable region comprising HVR-L1 comprising the amino acid sequence RASQDIHTYLN (SEQ ID NO:4), HVR-L2 comprising the amino acid sequence YTSRLHS (SEQ ID NO:5), and HVR-L3 comprising the amino acid sequence QQVSSLPPWT (SEQ ID NO:6).

In some embodiments, the anti-PD-L1 antibody comprises one, two, three, four, five or six HVRs (Kabat) of antibody 14D3, e.g., as shown in FIG. 1A and FIG. 1B. In some embodiments, the anti-PD-L1 antibody comprises the VH and/or VL of antibody 14D3, e.g., as shown in FIG. 1A AND FIG. 1B.

In some embodiments, anti-PD-L1 antibody is provided, wherein the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 7. In certain embodiments, a VH sequence having at least 90%, 91%, 92%, 93%, 94%, 95%, 96%, 97%, 98%, 99%, or 100% sequence identity to the amino acid sequence of SEQ ID NO: 7 contains substitutions (e.g., conservative substitutions), insertions, or deletions relative to the reference sequence, but an anti-PD-L1 antibody comprising that VH sequence retains the ability to bind to PD-L1. In certain embodiments, a total of 1 to 10 amino acids have been substituted, inserted and/or deleted in SEQ ID NO: 7. In certain embodiments, substitutions, insertions, or deletions occur in regions outside the HVRs (i.e., in the FRs). Optionally, the anti-PD-L1 antibody comprises the VH sequence of SEQ ID NO: 7 including post-translational modifications of that sequence. In a particular embodiment, the VH comprises one, two or three HVRs selected from: (a) HVR-H1 comprising the amino acid sequence of SEQ ID NO: 1, (b) HVR-H2 comprising the amino acid sequence of SEQ ID NO: 2, and (c) HVR-H3 comprising the amino acid sequence of SEQ ID NO: 3.

In some embodiments, anti-PD-L1 antibody is provided, wherein the antibody comprises, a light chain variable domain (VL) having at least 90%, 91%, 92%, 93%, 94%, 95%, 96%, 97%, 98%, 99%, or 100% sequence identity to the amino acid sequence of SEQ ID NO: 8. In certain embodiments, a VL sequence having at least 90%, 91%, 92%, 93%, 94%, 95%, 96%, 97%, 98%, 99%, or 100% sequence identity to the amino acid sequence of SEQ ID NO: 8 contains substitutions (e.g., conservative substitutions), insertions, or deletions relative to the reference sequence, but an anti-PD-L1 antibody comprising that VL sequence retains the ability to bind to the PD-L1 antibody. In certain embodiments, a total of 1 to 10 amino acids have been substituted, inserted and/or deleted in SEQ ID NO: 8. In certain embodiments, the substitutions, insertions, or deletions occur in regions outside the HVRs (i.e., in the FRs). Optionally, the anti-PD-L1 antibody comprises the VL sequence of SEQ ID NO: 8, including post-translational modifications of that sequence. In a particular embodiment, the VL comprises one, two or three HVRs selected from (a) HVR-L1 comprising the amino acid sequence of SEQ ID NO: 4; (b) HVR-L2 comprising the amino acid sequence of SEQ ID NO: 5; and (c) HVR-L3 comprising the amino acid sequence of SEQ ID NO: 6.

In another aspect, an anti-PD-L1 antibody is provided, wherein the antibody comprises a VH as in any of the embodiments provided above, and a VL as in any of the embodiments provided above. In one embodiment, the antibody comprises the VH sequence of SEQ ID NO: 7 and the VL sequence of SEQ ID NO: 8, including post-translational modifications of those sequences.

In another aspect, an anti-PD-L1 antibody is provided, wherein the antibody comprises a heavy chain as in any of the embodiments provided above, and a light chain as in any of the embodiments provided above. In one embodiment, the antibody comprises the heavy chain sequence of SEQ ID NO: 9 and the light chain sequence of SEQ ID NO: 10, including post-translational modifications of those sequences.

Antibodies of the present invention may also be described or specified in terms of their binding affinity to PD-L1 (for example human PD-L1). Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In a further aspect of the invention, an anti-PD-L1 antibody according to any of the above embodiments is a monoclonal antibody, including a chimeric, humanized or mouse antibody. In one embodiment, an anti-PD-L1 antibody is an antibody fragment, e.g., a Fv, Fab, Fab', scFv, diabody, or F(ab')$_2$ fragment. In another embodiment, the anti-PD-L1 antibody is a full length antibody, e.g., an intact IgG1 antibody or other antibody class or isotype as defined herein.

In a further aspect of the invention, an anti-PD-L1 antibody according to any of the above embodiments or described herein is linked or conjugated to a heterologous moiety or a detectable moiety. In some embodiments, the detectable moiety is a label or biotin. In some embodiments, the detectable moiety is a label. In some embodiments, the detectable moiety is biotin. In some embodiments, the detectable moiety is a fluorophore. In some embodiments, the fluorophore is R-phycoerythrin (PE), PE-Cy7, Alexa Fluor 488, fluorescein isothiocyanate (FITC), peridinin chlorophyll protein complex (PerCP), BV421, BV510, APC-H7, Alexa Fluor 647, or allophycocyanin (APC). In some embodiments, the fluorophore is R-phycoerythrin (PE). In some embodiments, the fluorophore is allophycocyanin (APC). In some embodiments, the fluorophore is Alexa Fluor 647.

Anti-PD-L1 Antibody Heavy Chain Variable Region Amino Acid Sequence (SEQ ID NO: 7)
QVQLQQSGPELVNPGASVKISCKASGYAFSTSWMNWVKQRPGKGLEWI

GRIYPRDGDTYYNGKFKDKATLTADKSSNTAYMQLSSLTSEDSAVYFC

TKNPGGYYFDYWGQGTTLTVSS

Anti-PD-L1 Antibody Light Chain Variable Region Amino Acid Sequence (SEQ ID NO: 8)
DIQMTQTTSSLSASLGDRVTINCRASQDIHTYLNWYQQKPDGTVKLLI

FYTSRLHSGVPSRFSGSGSGTDYSLTISNLEQEDIATYFCQQVSSLPP

WTFGGGTKVEIK

Anti-PD-L1 Antibody Heavy Chain Amino Acid Sequence (SEQ ID NO: 9)
QVQLQQSGPELVNPGASVKISCKASGYAFSTSWMNWVKQRPGKGLEWI

GRIYPRDGDTYYNGKFKDKATLTADKSSNTAYMQLSSLTSEDSAVYFC

TKNPGGYYFDYWGQGTTLTVSSASTKGPSVYPLAPVCGDTTGSSVTLG

CLVKGYFPEPVTLTWNSGSLSSGVHTFPAVLQSDLYTLSSSVTVTSST

WPSQSITCNVAHPASSTKVDKKIEPRGPTIKPCPPCKCPAPNLLGGPS

VFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERT

ISKPKGSVRAPQVYVLPPPEEEMTKKQVTLTCMVTDFMPEDIYVEWTN

NGKTELNYKNTEPVLDSDGSYFMYSKLRVEKKNWVERNSYSCSVVHEG

LHNHHTTKSFSRTPG

Anti-PD-L1 Antibody Light Chain Amino Acid Sequence (SEQ ID NO: 10)
DIQMTQTTSSLSASLGDRVTINCRASQDIHTYLNWYQQKPDGTVKLLI

FYTSRLHSGVPSRFSGSGSGTDYSLTISNLEQEDIATYFCQQVSSLPP

WTFGGGTKVEIKRADAAPTVSIFPPSSEQLTSGGASVVCFLNNFYPKD

INVKWKIDGSERQNGVLNSWTDQDSKDSTYSMSSTLTLTKDEYERHNS

YTCEATHKTSTSPIVKSFNRNEC

B. Reference or Therapeutic Anti-PD-L1 Antibodies

In another aspect, an anti-PD-L1 antibody described herein does not cross-compete for binding to PD-L1 with a reference anti-PD-L1 antibody or therapeutic anti-PD-L1 antibody. The terms "reference anti-PD-L1 antibody" and "therapeutic anti-PD-L1 antibody" as used herein refer to an anti-PD-L1 antibody other than an anti-PD-L1 of the present disclosure. The terms "reference anti-PD-L1 antibody" and "therapeutic anti-PD-L1 antibody" can be used interchangeably, but the term "therapeutic anti-PD-L1 antibody" is generally used when the antibody is administered to a subject.

In certain embodiments the reference or therapeutic anti-PD-L1 antibody comprises (a) a heavy chain variable region comprising HVR-H1 comprising the amino acid sequence GFTFSDSWIH (SEQ ID NO: 11), HVR-H2 comprising the amino acid sequence AWISPYGGSTYYADSVKG (SEQ ID NO: 12) and HVR-H3 comprising the amino acid sequence RHWPGGFDY (SEQ ID NO:13); and (b) a light chain variable region comprising HVR-L1 comprising the amino acid sequence RASQDVSTAVA (SEQ ID NO: 14), HVR-L2 comprising the amino acid sequence SASFLYS (SEQ ID NO:15), and HVR-L3 comprising the amino acid sequence QQYLYHPAT (SEQ ID NO: 16).

In some embodiments, the reference or therapeutic anti-PD-L1 antibody comprises a heavy chain variable region comprising the amino acid sequence of SEQ ID NO: 17, and a light chain variable region comprising the amino acid sequence of SEQ ID NO: 18. In some embodiments, the anti-PD-L1 antibody comprises a heavy chain variable region having at least 85%, 86%, 87%, 88%, 89%, 90%, 91%, 92%, 93%, 94%, 95%, 96%, 97%, 98%, or 99% sequence identity to the heavy chain variable region having the amino acid sequence of SEQ ID NO: 17, and/or a light chain variable region having at least 85%, 86%, 87%, 88%, 89%, 90%, 91%, 92%, 93%, 94%, 95%, 96%, 97%, 98%, or 99% identity to the light chain variable region having the amino acid sequence of SEQ ID NO:18.

In some embodiments, the reference or therapeutic anti-PD-L1 antibody comprises a heavy chain comprising the amino acid sequence of SEQ ID NO: 19, and a light comprising the amino acid sequence of SEQ ID NO: 20. In some embodiments, the anti-PD-L1 antibody comprises a heavy chain having at least 85%, 86%, 87%, 88%, 89%, 90%, 91%, 92%, 93%, 94%, 95%, 96%, 97%, 98%, or 99% sequence identity to the heavy chain having the amino acid sequence of SEQ ID NO: 19, and a light chain having at least 85%, 86%, 87%, 88%, 89%, 90%, 91%, 92%, 93%, 94%, 95%, 96%, 97%, 98%, or 99% identity to the light chain having the amino acid sequence of SEQ ID NO:20.

In some embodiments, the reference or therapeutic anti-PD-L1 antibody is atezolizumab (TECENTRIQ®).

In some embodiments, the reference or therapeutic anti-PD-L1 antibody is monoclonal, chimeric or humanized.

Exemplary Reference or Therapeutic Anti-PD-L1 Antibody Heavy Chain Variable Region Amino Acid Sequence:

```
                                        (SEQ ID NO: 17)
EVQLVESGGGLVQPGGSLRLSCAASGFTFSDSWIHWVRQAPGKGLEWV

AWISPYGGSTYYADSVKGRFTISADTSKNTAYLQMNSLRAEDTAVYYC

ARRHWPGGFDYWGQGTLVTVSS
```

Exemplary Reference or Therapeutic Anti-PD-L1 Antibody Light Chain Variable Region Amino Acid Sequence:

```
                                        (SEQ ID NO: 18)
DIQMTQSPSSLSASVGDRVTITCRASQDVSTAVAWYQQKPGKAPKLLI

YSASFLYSGVPSRFSGSGSGTDFTLTISSLQPEDFATYYCQQYLHPA

TFGQGTKVEIK
```

Exemplary Reference or Therapeutic Anti-PD-L1 Antibody Heavy Chain Amino Acid Sequence:

```
                                        (SEQ ID NO: 19)
EVQLVESGGGLVQPGGSLRLSCAASGFTFSDSWIHWVRQAPGKGLEWV

AWISPYGGSTYYADSVKGRFTISADTSKNTAYLQMNSLRAEDTAVYYC

ARRHWPGGFDYWGQGTLVTVSSASTKGPSVFPLAPSSKSTSGGTAALG

CLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNA

KTKPREEQYASTYRVVSVLTVLHQDWLNGKEYKCKVSNKALPAPIEKT

ISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEA

LHNHYTQKSLSLSPG
```

Exemplary Reference or Therapeutic Anti-PD-L1 Antibody Light Chain Amino Acid Sequence:

```
                                        (SEQ ID NO: 20)
DIQMTQSPSSLSASVGDRVTITCRASQDVSTAVAWYQQKPGKAPKLLI

YSASFLYSGVPSRFSGSGSGTDFTLTISSLQPEDFATYYCQQYLHPA

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

C. Methods of Production

A description follows as to exemplary techniques for the production of the anti-antibodies used in accordance with the present invention.

i. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include anti-PD-L1, an antigen binding fragment thereof, or fusion proteins thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for anti-PD-L1 antibody titer. If desired, the mammal can be boosted until the antibody titer increases or plateaus.

ii. Monoclonal Antibodies

The antibodies of the invention may alternatively be monoclonal antibodies. Monoclonal antibodies may be made using the hybridoma method first described by Kohler et al., Nature, 256:495 (1975), or may be made by recombinant DNA methods (see, e.g. U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium contains one or more substances that inhibit the growth or survival of the unfused, parental myeloma cells (also referred to as fusion partner). For example, if the parental myclonia cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Fusion partner myeloma cells are those that fuse efficiently, support stable high-level production of antibody by the selected antibody-producing cells, and are sensitive to a selective medium that selects against the unfused parental cells. Myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107: 220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology. 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994).

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Screening of the libraries can be accomplished by various techniques known in the art. For example, PD-L1 can be used to coat the wells of adsorption plates, expressed on host cells affixed to adsorption plates or used in cell sorting, or conjugated to biotin for capture with streptavidin-coated beads, or used in any other method for panning display libraries.

The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

Any of the anti-PD-L1 antibodies of the invention can be obtained by designing a suitable antigen screening procedure to select for the phage clone of interest followed by construction of a full length anti-PD-L1 antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

iii. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

1. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207: 179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 hydrophobic: Norlecucinc, Met, Ala, Val, Leu, Ile;
 neutral hydrophilic: Cys, Ser, Thr, Asn, Gln;
 acidic: Asp, Glu;
 basic: His, Lys, Arg;
 residues that influence chain orientation: Gly, Pro;
 aromatic: Trp, Tyr, Phe.

Non-conservative substitutions will entail exchanging a member of one of these classes for another class.

One type of substitutional variant involves substituting one or more hypervariable region residues of a parent antibody (e.g. a mouse, humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions.

Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

iv. Recombinant Methods and Compositions

Antibodies may be produced using recombinant methods and compositions, e.g., as described in U.S. Pat. No. 4,816,567. In one embodiment, isolated nucleic acid encoding an anti-PD-L1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an anti-PD-L1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-PD-L1 antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040, 498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV 1 line transformed by SV40 (COS-7); human embryonic kidney line (293 or 293 cells as described, e.g., in Graham et al., J Gen Viral. 36:59 (1977); baby hamster kidney cells (BHK); mouse sertoli cells (TM4 cells as described, e.g., in Mather, Biol. Reprod. 23:243-251 (1980); monkey kidney cells (CV 1); African green monkey kidney cells (VERO-76); human cervical carcinoma cells (HELA); canine kidney cells (MOCK; buffalo rat liver cells (BRL 3A); human lung cells (W138); human liver cells (Hep 02); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFK CHO cells (Urlaub ct al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

III. Assays

Anti-PD-L1 antibodies provided herein may be identified, screened for, or characterized for their physical/chemical properties and/or biological activities by various assays known in the art.

A. Binding Assays and Other Assays

In one aspect, an antibody of the invention is tested for its antigen binding activity, e.g., by known methods such as ELISA, Western blot, etc. Binding affinity can be measured by common methods known in the art. In one embodiment, the $K_D$ of an antibody is measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol. Biol* 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the $K_D$ is measured by using surface-plasmon resonance assays using a BIACORE®-2000 or a BIACORE®-3000 instrument (BIAcore, Inc., Piscataway, N.J.) at 25° C. with immobilized antigen CM5 chips at 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (0.2 μM) before injection at a flow rate of 5 μL/minute to achieve approximately 10 response units (RU) of the coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 μL/min. Association rates ($k_{on}$) and dissociation rates ($k_{off}$) are calculated using a simple one-to-one *Langmuir* binding model (BIAcore® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

In another aspect, competition assays may be used to determine whether an anti-PD-L1 antibody described herein competes for binding to PD-L1 with a therapeutic or reference antibody as described herein. In certain embodiments, the competition assay used to determine whether an anti-PD-L1 antibody described herein competes for binding to PD-L1 with a therapeutic or reference antibody as described herein is flow cytometry. In certain embodiments, such a competing antibody binds to the same epitope (e.g., a linear or a conformational epitope) of PD-L1. Detailed exemplary methods for mapping an epitope to which an antibody binds are provided in Morris (1996) "Epitope Mapping Protocols," in Methods in Molecular Biology vol. Humana Press, Totowa, N.J.). In some embodiments, an anti-PD-L1 antibody described herein does not compete for binding to PD-L1 with a therapeutic or reference antibody as described herein. In some embodiments, an anti-PD-L antibody that does not compete for binding to PD-L1 with a therapeutic or reference antibody as described herein if the antibody blocks binding of the therapeutic or reference antibody to PD-L1 in a competition assay by less than 20%, less than 15%, less than 10%, less than 9%, less than 8%, less than 7%, less than 6%, less than 5%, less than 4%, less than 3%, less than 2%, less than 1%. In some embodiments, an anti-PD-L1 antibody that competes for binding to PD-L1 with a therapeutic or reference antibody as described herein if the antibody blocks binding of the therapeutic or reference antibody to PD-L1 in a competition assay by more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%. In some embodiments, the PD-L1 is human PD-L1.

In an exemplary competition assay, immobilized PD-L1 is incubated in a solution comprising a first labeled antibody (e.g., a first labeled anti-PD-L1 antibody) that binds to PD-L1 antibody, and a second unlabeled antibody (e.g., a second unlabeled anti-PD-L1 antibody) that is being tested for its ability to compete with the first antibody for binding to PD-L1. The second antibody may be present in a hybridoma supernatant. As a control, immobilized PD-L1 is incubated in a solution comprising the first labeled antibody but not the second unlabeled antibody. After incubation under conditions permissive for binding of the first antibody to PD-L1, excess unbound antibody is removed, and the amount of label associated with immobilized PD-L1 is measured. If the amount of label associated with immobilized PD-L1 is substantially reduced in the test sample relative to the control sample, then that indicates that the second antibody is competing with the first antibody for binding to PD-L1. See Harlow and Lane (1988) Antibodies: A Laboratory Manual ch. 14 (Cold Spring Harbor Laboratory, Cold Spring Harbor, N.Y.). Competition assays can also be performed in a manner as described above with FACS using cells transfected with PD-L1 and expressed on the cell surface. Additionally, ELISA with PD-L1 can also be used in a competition assay. In some embodiments, the competition assay is flow cytometry.

IV. Methods of Using Anti-PD-L1 Antibodies

Certain aspects of the present disclosure relate to methods of detecting or quantifying the level of expression of human PD-L1 in a biological sample, e.g., from a subject having cancer to assess, for example, responsiveness of the subject to therapeutic anti-PD-L1 antibody treatment. As disclosed herein and without wishing to be bound by theory, expression levels of PD-L1, for example levels of human PD-L1 expressed on the surface of cells in a biological sample, can be used in the diagnosis of cancer (e.g., a PD-L1-expressing cancer) and to assess responsiveness to a cancer therapy (e.g., treatment with a therapeutic anti-PD-L1 antibody). As disclosed herein, anti-PD-L1 antibodies of the present disclosure do not compete with therapeutic anti-PD-L1 antibodies (e.g., atezolizumab) for binding to human PD-L1 (see, Examples 1 and 2). Advantageously, anti-PD-L1 antibodies of the present disclosure can be used to quantify PD-L1 expression from immune and tumor cells and in the presence of a therapeutic anti-PD-L1 antibody, such as atezolizumab using, for example, a flow cytometry assay. This is in contrast to other commercially available anti-PD- L1 antibodies, such as PD-L1 clone 29E.23, which compete with therapeutic anti-PD-L1 antibodies (e.g., atezolizumab) for binding to human anti-PD-L1, which thus prevents their use in quantifying PD-L1 expression on the surface of immune and tumor cells.

The methods of the present disclosure may be used, inter alia, to modulate/adjust/determine/select the dosing of a subject having cancer who will be/has been/is being treated with a therapeutic anti-PD-L1 antibody, to select a subject having cancer for treatment with a therapeutic anti-PD-L1 antibody, to assess the responsiveness of a subject to a therapeutic anti-PD-L1 antibody, to assess progression-free survival of a subject having cancer and treated with a therapeutic anti-PD-L1 antibody, to assess tumor burden in a subject having cancer and treated with a therapeutic anti-PD-L1 antibody, to predict cancer progression in a subject having cancer and treated with a therapeutic anti-PD-L1 antibody, to diagnose a subject having a PD-L1-expressing cancer, to diagnose a subject having cancer that is responsive to treatment with a therapeutic anti-PD-L1 antibody, and to diagnose cancer progression in a subject having cancer and treated with a therapeutic anti-PD-L1 antibody. Examples of cancers may include, but are not limited to, multiple myeloma, myelodysplastic syndrome, and/or acute myeloid leukemia. In some embodiments, the cancer is a PD-L1-expressing cancer.

Any of the anti-PD-L1 antibodies as provided herein are useful for detecting the presence of PD-L1 in a biological sample. In certain embodiments, any of the anti-PD-L1 antibodies as provided herein are useful to quantitate PD-L1 levels in a biological sample. In certain embodiments, any of the anti-PD-L1 antibodies as described herein are useful for detecting the presence of PD-L1 in a biological sample comprising immune cells. In certain embodiments, any of the anti-PD-L antibodies as described herein are useful for detecting the presence of PD-L1 in a biological sample comprising tumor cells. In certain embodiments, any of the anti-PD-L1 antibodies as described herein are useful for detecting the presence of PD-L1 in a biological sample comprising live cells. In certain embodiments, any of the anti-PD-L1 antibodies as described herein are useful for detecting the presence of PD-L1 in a biological sample, wherein the biological sample is from a subject that has been treated with a therapeutic anti-PD-L1 antibody. In certain embodiments, any of the anti-PD-L1 antibodies as provided herein are useful for detecting the presence of PD-L1 in a biological sample using, for example, flow cytometry, immunoassay (for example ELISA-based assays and proximity extension assays), Western blotting, peptide microarray, immunohistochemistry, and/or mass spectrometry. In certain embodiments, any of the anti-PD-L1 antibodies as provided herein are useful for detecting the presence of PD-L1 in a biological sample, wherein the biological sample is a blood sample. In certain embodiments, any of the anti-PD-L1 antibodies as provided herein are useful for detecting the presence of PD-L1 in a biological sample, wherein the biological sample is a bone marrow sample.

Detection Labels

In some embodiments, the anti-PD-L1 antibody is conjugated with any label moiety which can be covalently attached to the antibody through a reactive moiety, an activated moiety, or a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.). In some embodiments, the fluorophore is R-phycoerythrin (PE), PE-Cy7, Alexa Fluor 488, fluorescein isothiocyanate (FITC), peridinin chlorophyll protein complex (PerCP), BV421, BV510, APC-H7, Alexa Fluor 647 or allophycocyanin (APC). In some embodiments, the fluorophore is R-phycoerythrin (PE). In some embodiments, the fluorophore is PE-Cy7. In some embodiments, the fluorophore is Alexa Fluor 488. In some embodiments, the fluorophore is fluorescein isothiocyanate (FITC). In some embodiments, the fluorophore is peridinin chlorophyll protein complex (PerCP). In some embodiments, the fluorophore is BV421. In some embodiments, the fluorophore is BV510. In some embodiments, the fluorophore is APC-H7. In some embodiments, the fluorophore is Alexa Fluor 647. In some embodiments, the fluorophore is allophycocyanin (APC).

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

Radioisotopes (radionuclides), such as $^{3}$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{77}$Lu, $^{211}$At, or $^{213}$Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targetted via complexation with the antibody-drug conjugates of the invention (Wu et al (2005) Nature Biotechnology 23(9):1137-1146).

Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al ((2000) Proc. Natl. Acad. Sci. USA 97(4): 1802-1807). DOTA-maleimide reagents react with the free cysteine amino acids of the cysteine engineered antibodies and provide a metal complexing ligand on the antibody (Lewis et al (1998) Bioconj.

Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Metal-chelate complexes suitable as antibody labels for imaging experiments are disclosed: U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo ct al (1998) Clinical Cancer Research 4:2483-90; Blend ct al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidasc, micropcroxidasc, and the like. Techniques for conjugating enzymes to antibodies are described in O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166. Examples of enzyme-substrate combinations include, for example: (i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); (ii)alkaline phosphatase (AP) with para-nitrophenyl phosphate as chromogenic substrate; and (iii) β-D-galactosidase (β-D-Gal) with a chromogenic substrate (e.g., p-nitrophenyl-3-D-galactosidase) or fluorogenic substrate 4-methylumbelliferyl-β-D-galactosidase. Numerous other enzyme-substrate combinations are available to those skilled in the art. For a general review, see U.S. Pat. Nos. 4,275,149 and 4,318,980.

A label may be indirectly conjugated with an amino acid side chain, an activated amino acid side chain, a cysteine engineered antibody, and the like. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, inmmunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled anti-PD-L1 antibodies of the present disclosure may be useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of atherapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Biological Samples

In certain embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body. In certain embodiments, the biological sample is a peripheral blood sample. In certain embodiments, the biological sample is a bone marrow sample. In certain embodiments, a biological sample is a cancer sample. In certain embodiments, a biological sample is a tumor biopsy. In various embodiments, the sample is a body sample from any animal. In various embodiments, the sample is a sample from a human. In certain embodiments, the sample comprises live cells. In certain embodiments, the sample comprises immune cells. In certain embodiments, the sample comprises tumor cells.

Accordingly, certain aspects of the present disclosure relate to methods for detecting PD-L1 in a biological sample obtained from a subject include the step of contacting the biological sample with an antibody or antigen-binding fragment as described herein and detecting binding of the antibody or antigen-binding fragment to PD-L1 in the biological sample, thereby detecting PD-L1 in the biological sample. In some embodiments, the antibody or antigen-binding fragment is detected using flow cytometry, an immunoassay (for example ELISA-based assays and proximity extension assays), Western blotting, peptide microarray, immunohistochemistry, and/or mass spectrometry. In certain embodiments, the antibody or antigen-binding fragment is detected using flow cytometry. In some embodiments, the biological sample is a blood sample. In some embodiments, the biological sample is a bone marrow sample. In some embodiments, the biological sample is a cell or tissue. In some embodiments, the cell or tissue is a cancerous cell or cancerous tissue. In some embodiments, the biological sample comprises live cells. In some embodiments, the subject has a cancer. In some embodiments, the cancer is a PD-L1-expressing cancer. In some embodiments, the cancer is multiple myeloma, myelodysplastic syndrome, and/or acute myeloid leukemia. In some embodiments, the biological sample is obtained from a subject that has been administered a therapeutic anti-PD-L1 antibody or antigen-binding fragment thereof of the present disclosure. In some embodiments, the therapeutic anti-PD-L1 antibody comprises a heavy chain variable region comprising the three HVR (HVR-H1, HVR-H2, and HVR-H3) amino acid sequences of atezolizumab and a light chain variable region comprising the three HVR (HVR-L1, HVR-L2, and HVR-L3) amino acid sequences of atezolizumab. In some embodiments, the therapeutic anti-PD-L1 antibody comprises the heavy chain variable region amino acid sequence of atezolizumab and the light chain variable region amino acid sequence of atezolizumab. In some embodiments, the therapeutic anti-PD-L1 antibody comprises the heavy chain amino acid sequence of atezolizumab and the light chain amino acid sequence of atezolizumab. In some embodiments, the therapeutic anti-PD-L1 antibody is atezolizumab. In some embodiments, the subject is a human.

Predicting/Monitoring/Assessing Responsiveness

In certain embodiments, the methods of the present disclosure relate to methods for monitoring cancer treatment in a subject by contacting a first biological sample with an anti-PD-L1 antibody or antigen-binding fragment of the present disclosure; detecting binding of the antibody or antigen-binding fragment to PD-L1 in the first biological sample; determining the amount of PD-L1 present in the first biological sample; contacting a second biological sample with an anti-PD-L1 antibody or antigen-binding fragment of the present disclosure, wherein the second biological sample is obtained after treatment with a therapeutic anti-PD-L1 antibody or antigen-binding fragment thereof (e.g., atezolizumab); detecting binding of the antibody or antigen-binding fragment to PD-L1 in the second biological sample; determining the amount of PD-L1 present in the second biological sample; determining the amount of PD-L1 present in the second biological sample; and comparing the amount of PD-L1 present in the first biological sample to the amount of PD-L1 present in the second biological sample.

In some embodiments, an increase in the amount of PD-L1 present in the second biological sample compared to the first biological sample indicates that the subject is not responding to treatment with the therapeutic anti-PD-L1 antibody. In some embodiments, an increase of at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% in the amount of PD-L1 present in the second biological sample compared to the first biological sample indicates the subject is non-responsive to the therapeutic anti-PD-L1 antibody (e.g., atezolizumab).

In some embodiments, a decrease in the amount of PD-L1 present in the second biological sample compared to the first biological sample indicates that the subject is responding to treatment with the therapeutic anti-PD-L1 antibody. In some embodiments, a decrease of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the amount of PD-L1 present in the second biological sample compared to the first biological sample indicates that the subject is responding to treatment with the therapeutic anti-PD-L1 antibody (e.g., atezolizumab).

In some embodiments, the first biological sample is obtained from the subject prior to treatment with the therapeutic anti-PD-L1 antibody or antigen-binding fragment thereof. In some embodiments, the first biological sample is obtained from the subject after treatment with the therapeutic anti-PD-L1 antibody or antigen-binding fragment thereof. In some embodiments, the first and second biological samples are blood samples. In some embodiments, the first and second biological samples are bone marrow samples. In some embodiments, the first and second biological samples are cells or tissues. In some embodiments, the cells or tissues are cancerous cells or cancerous tissues. In some embodiments, the first and second biological samples comprise live cells. In some embodiments, the subject has a cancer is multiple myeloma, myelodysplastic syndrome, and/or acute myeloid leukemia. In some embodiments, the subject has a cancer. In some embodiments, the cancer is a PD-L1-expressing cancer. In some embodiments, the cancer is multiple myeloma, myelodysplastic syndrome, and/or acute myeloid leukemia. In some embodiments, the biological sample is obtained from a subject that has been administered a therapeutic anti-PD-L1 antibody or antigen-binding fragment thereof of the present disclosure. In some embodiments, the therapeutic anti-PD-L1 antibody comprises a heavy chain variable region comprising the three HVR (HVR-H1, HVR-H2, and HVR-H3) amino acid sequences of atezolizumab and a light chain variable region comprising the three HVR (H-VR-L1, HVR-L2, and HVR-L3) amino acid sequences of atezolizumab. In some embodiments, the therapeutic anti-PD-L1 antibody comprises the heavy chain variable region amino acid sequence of atezolizumab and the light chain variable region amino acid sequence of atezolizumab. In some embodiments, the therapeutic anti-PD-L1 antibody comprises the heavy chain amino acid sequence of atezolizumab and the light chain amino acid sequence of atezolizumab. In some embodiments, the therapeutic anti-PD-L1 antibody is atezolizumab. In some embodiments, the antibody or antigen-binding fragment is detected using flow cytometry, an immunoassay (for example ELISA-based assays and proximity extension assays), Western blotting, peptide microarray, immunohistochemistry, and/or mass spectrometry. In certain embodiments, the antibody or antigen-binding fragment is detected using flow cytometry. In some embodiments, the subject is a human.

In certain embodiments, the methods of the present disclosure relate to methods for assessing, monitoring, or predicting responsiveness of a subject having cancer (e.g., a PD-L1-expressing cancer) to treatment with a therapeutic anti-PD-L1 antibody (e.g., atezolizumab). In some embodiments, the method comprises measuring or detecting the level of expression of PD-L1 in a sample obtained from a subject at a first time point, and measuring or detecting the level of expression of PD-L1 in a sample obtained from a subject at a second time point. In some embodiments, the second time point is after administration of the therapeutic anti-PD-L1 antibody. In some embodiments, the subject has never received the therapeutic anti-PD-L1 antibody. In some embodiments, the subject is undergoing treatment with a therapeutic anti-PD-L1 antibody.

In some embodiments, the method comprises measuring or detecting the level of expression of PD-L1 in a sample obtained from a subject at a first time point, administering to the subject a therapeutically effective amount of a therapeutic anti-PD-L1 antibody (e.g., atezolizumab), and measuring or detecting the level of expression of PD-L1 in a sample obtained from a subject at a second time. In some embodiments, the first time point is prior to administering to the subject a therapeutic anti-PD-L1 antibody. In some embodiments, the second time point is after administration of the therapeutic anti-PD-L1 antibody. In some embodiments, the subject has never received the therapeutic anti-PD-L1 antibody. In some embodiments, the subject is undergoing treatment with a therapeutic anti-PD-L1 antibody.

In some embodiments, the method comprises classifying the subject as responsive or non-responsive to treatment with the therapeutic anti-PD-L1 antibody based on the level of expression of PD-L1 in the sample obtained from the subject at the second time point, as compared to the first time point, where decreased level of expression of PD-L1 at the second time point indicates the subject is or may be responsive to treatment with the therapeutic anti-PD-L1 antibody (e.g., atezolizumab).

In some embodiments, a decrease of less than 25%, less than 20%, less than 15%, less than 10%, less than 9%, less than 8%, less than 7%, less than 6%, less than 5%, less than 4%, less than 3%, less than 2%, less than 1%, no decrease, or an increase of greater than 1%, greater than 2%, greater than 3%, greater than 4%, greater than 5%, greater than 10%, greater than 5%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100% in the level of expression of PD-L1 from the first time point to the second time point indicates the subject is non-responsive to the therapeutic anti-PD-L1 antibody (e.g., atezolizumab). In some embodiments, no decrease in the level of expression of PD-L1 from the first time point to the second time point indicates the subject is non-responsive to the therapeutic anti-PD-L1 antibody. In some embodiments, an increase in the level of expression of PD-L1 from the first time point to the second time point indicates the subject is non-responsive to the therapeutic anti-PD-L1 antibody.

In some embodiments, a decrease of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the level of expression of PD-L1 from the first time point to the second time point indicates the subject is responsive to the therapeutic anti-PD-L1 antibody (e.g., atezolizumab).

In some embodiments, responsiveness may refer to treatment efficacy. It will be appreciated by one of skill in the art that many measures of treatment efficacy, and combinations thereof, may be useful. In some embodiments, treatment efficacy may include a tumor response (e.g., a stabilization or reduction in tumor size, growth, or histological stage). In some embodiments, treatment efficacy may include increased survival (e.g., one-year, 5-year, disease-free, or overall), increased quality of life, increased time to progression, or decreased morbidity. Such factors may be assessed, e.g., by using a statistical tool such as logistic regression, Cox's proportional hazards regression, or Kaplan-Meier estimates.

Continuing/Discontinuing/Modulating Treatment

As disclosed herein, a measurement of the level of expression of PD-L1 in a sample from a subject after administration of a therapeutic anti-PD-L antibody (e.g., Atczolizumab) may be used to guide subsequent treatment, for example, continuing the therapeutic anti-PD-L1 antibody treatment, discontinuing the therapeutic anti-PD-L1 antibody treatment, or modulating the therapeutic anti-PD-L1 antibody treatment. Accordingly, in certain embodiments, the methods of the present disclosure relate to methods for modulating treatment with a therapeutic anti-PD-L1 antibody (e.g., atezolizumab) in a subject having cancer (e.g., a PD-L1-expressing cancer). In some embodiments, the method comprises measuring or detecting the level of expression of PD-L1 in a sample obtained from the subject at a first time point, administering to the subject a therapeutically effective amount of a therapeutic anti-PD-L1 antibody, measuring or detecting the level of expression of PD-L1 in a sample obtained from the subject at a second time point, and modulating the amount of therapeutic anti-PD-L1 antibody administered to the subject based on the changes in the level of expression of PD-L1 between the first and second time points. In some embodiments, the first time point is prior to administering to the subject a therapeutic anti-PD-L1 antibody. In some embodiments, the second time point is after administration of the therapeutic anti-PD-L1 antibody.

In some embodiments, modulating the amount of therapeutic anti-PD-L1 antibody administered to the subject comprises maintaining the same level of therapeutic anti-PD-L1 antibody administered to the subject.

In some embodiments, modulating the amount of therapeutic anti-PD-L1 antibody administered to the subject comprises increasing the level of therapeutic anti-PD-L1 antibody administered to the subject. An increase in the level of therapeutic anti-PD-L1 antibody administered to the subject may refer without limitation to one or more of: increasing the amount, dose, number or frequency of doses, or concentration of the therapeutic anti-PD-L1 antibody administered to the subject.

In some embodiments, modulating the amount of therapeutic anti-PD-L1 antibody administered to the subject comprises decreasing the level of therapeutic anti-PD-L1 antibody administered to the subject. A decrease in the level of therapeutic anti-PD-L1 antibody administered to the subject may refer without limitation to one or more of: decreasing the amount, dose, number or frequency of doses, or concentration of the therapeutic anti-PD-L1 antibody administered to the subject.

Predicting Cancer Progression

In certain embodiments, the methods of the present disclosure relate to methods for assessing progression-free survival in a subject having cancer (e.g., a PD-L1-expressing cancer). In some embodiments, the method comprises measuring or detecting the level of expression of PD-L1 in a sample obtained from the subject at a first time point, administering to the subject a therapeutically effective amount of a therapeutic anti-PD-L1 antibody (e.g., atezolizumab), and measuring or detecting the level of expression of PD-L1 in a sample obtained from the subject at a second time point. In some embodiments, the first time point is prior to administering to the subject a therapeutic anti-PD-L1 antibody. In some embodiments, the second time point is after administration of the therapeutic anti-PD-L1 antibody.

In some embodiments, a decrease of at least 10%, at least 15%, at least 200%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the level of expression of PD-L1 from the first time point to the second time point indicates the therapeutic anti-PD-L1 antibody increases progression-free survival.

Also provided herein are methods for predicting cancer progression in a subject having a PD-L1-expressing cancer. In some embodiments, the method comprises measuring or detecting the level of expression of PD-L1 in a sample obtained from the subject at a first time point, administering to the subject a therapeutically effective amount of a therapeutic anti-PD-L1 antibody (e.g., atezolizumab), and measuring or detecting the level of expression of PD-L1 in a sample obtained from the subject at a second time point. In some embodiments, the first time point is prior to administering to the subject a therapeutic anti-PD-L1 antibody. In some embodiments, the second time point is after administration of the therapeutic anti-PD-L1 antibody.

In some embodiments, a decrease of less than 25%, less than 20%, less than 15%, less than 10%, less than 9%, less than 8%, less than 7%, less than 6%, less than 5%, less than 4%, less than 3%, less than 2%, less than 10%, no decrease, or an increase of greater than 1%, greater than 2%, greater than 3%, greater than 4%, greater than 5%, greater than 10%, greater than 5%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100% in the level of expression of PD-L1 from the first time point to the second time point indicates the subject has a cancer that is likely to progress.

Time Point Measurements

In the methods of the present disclosure, the level of expression of PD-L1 is compared between a first time point (e.g., a baseline) and a second time point in a subject having cancer (e.g., a PD-L1-expressing cancer). In some embodiments, the subject has a PD-L1-expressing cancer.

In some embodiments, the first time point is used to detect the level of expression of PD-L1 in the subject prior to therapeutic anti-PD-L1 antibody (e.g., atezolizumab) treatment. For example, the level of expression of PD-L1 in a subject may be measured prior to therapeutic anti-PD-L1 antibody treatment, and one or more samples taken subsequent to treatment with a therapeutic anti-PD-L1 antibody may be used, inter alia, to monitor the efficacy of the treatment, determine whether to continue or discontinue the treatment, modulate the treatment, monitor responsiveness to the treatment, predict responsiveness to a maintenance treatment, predict cancer progression, and so forth.

In some embodiments, the first time point is used to measure or detect the level of expression of PD-L1 in the subject immediately before, or about 10 seconds before, about 30 seconds before, about 1 minute before, about 5 minutes before, about 10 minutes before, about 15 minutes before, about 30 minutes before, about 45 minutes before, about 1 hour before, about 1.5 hours before, about 2 hours before, about 2.5 hours before, about 3 hours before, about 3.5 hours before, about 4 hours before, about 4.5 hours before, about 5 hours before, about 5.5 hours before, about 6 hours before, about 7 hours before, about 8 hours before, about 9 hours before, about 10 hours before, about 11 hours before, about 12 hours before, about 18 hours before, about 1 day before, about 2 days before, about 3 days before, about 4 days before, about 5 days before, about 6 days before, about 1 week before, about 2 weeks before, about 3 weeks before, or about 4 weeks before therapeutic anti-PD-L1 antibody treatment. In some embodiments, the first time point is used to measure or detect the level of expression of PD-L1 in the subject about 1 hour before therapeutic anti-PD-L1 antibody treatment. In some embodiments, the first time point is used to measure or detect the level of expression of PD-L1 in the subject about 4 hours before therapeutic anti-PD-L1 antibody treatment. In some embodiments, the first time point is used to measure or detect the level of expression of PD-L1 in the subject about 1 day before therapeutic anti-PD-L1 antibody treatment. In some embodiments, the first time point is used to measure or detect the level of expression of PD-L1 in the subject about 3 days before therapeutic anti-PD-L1 antibody treatment. In specific embodiments, the therapeutic anti-PD-L1 antibody used in the treatment is atezolizumab.

In some embodiments, the first time point is used to measure or detect the level of expression of PD-L1 in the subject prior to therapeutic anti-PD-L1 antibody treatment, and can be compared with the level of expression of PD-L1 at a second time point. In some embodiments, the second time point is used to measure or detect the level of expression of PD-L1 in the subject after treatment with a therapeutic anti-PD-L1 antibody (e.g., a first time point can be taken before the initial dose of a therapeutically effective amount of a therapeutic anti-PD-L1 antibody and compared to a sample taken at a second time point, after the first, second, third, fourth, or later dose of the therapeutic anti-PD-L1 antibody). In some embodiments, the second time point is used to detect the level of expression of PD-L1 in the subject about 1 hour after, about 2 hours after, about 3 hours after, about 4 hours after, about 5 hours after, about 6 hours after, about 7 hours after, about 8 hours after, about 9 hours after, about 10 hours after, about 11 hours after, about 12 hours after, about 18 hours after, about 1 day after, about 1.5 days after, about 2 days after, about 2.5 days after, about 3 days after, about 3.5 days after, about 4 days after, about 4.5 days after, about 5 days after, about 5.5 days after, about 6 days after, about 6.5 days after, about 1 week after, about 1.5 weeks after, about 2 weeks after, about 2.5 weeks after, about 3 weeks after, about 3.5 weeks after, about 4 weeks after, about 1 month after, about 1.5 months after, about 2 months after, about 2.5 months after, about 3 months after, about 3.5 months after, about 4 months after, about 4.5 months after, about 5 months after, about 5.5 months after, about 6 months after, about 6.5 months after, about 7 months after, about 7.5 months after, about 8 months after, about 8.5 months after, about 9 months after, about 9.5 months after, about 10 months after, about 10.5 months after, about 11 months after, about 11.5 months after, or about 12 months after therapeutic anti-PD-L1 antibody treatment. In some embodiments, the second time point is used to detect the level of expression of PD-L1 in the subject about 1 hour after therapeutic anti-PD-L1 antibody treatment. In some embodiments, the second time point is used to detect the level of expression of PD-L1 in the subject about 4 hours after therapeutic anti-PD-L1 antibody treatment. In some embodiments, the second time point is used to detect the level of expression of PD-L1 in the subject about 8 hours after therapeutic anti-PD-L1 antibody treatment. In some embodiments, the second time point is used to detect the level of expression of PD-L1 in the subject about 12 hours after therapeutic anti-PD-L1 antibody treatment. In some embodiments, the second time point is used to detect the level of expression of PD-L1 in the subject about 18 hours after therapeutic anti-PD-L1 antibody treatment. In some embodiments, the second time point is used to detect the level of expression of PD-L1 in the subject about 1 day after therapeutic anti-PD-L1 antibody treatment. In some embodiments, the second time point is used to detect the level of expression of PD-L1 in the subject about 1.5 days after therapeutic anti-PD-L1 antibody treatment. In some embodiments, the second time point is used to detect the level of expression of PD-L1 in the subject about 2 days after therapeutic anti-PD-L1 antibody treatment. In some embodiments, the second time point is used to detect the level of expression of PD-L1 in the subject about 2.5 days after therapeutic anti-PD-L1 antibody treatment. In some embodiments, the second time point is used to detect the level of expression of PD-L1 in the subject about 3 days after therapeutic anti-PD-L1 antibody treatment. In some embodiments, the second time point is used to detect the level of expression of PD-L1 in the subject about 3.5 days after therapeutic anti-PD-L1 antibody treatment. In some embodiments, the second time point is used to detect the level of expression of PD-L1 in the subject about 4 days after therapeutic anti-PD-L1 antibody treatment. In some embodiments, the second time point is used to detect the level of expression of PD-L1 in the subject about 4.5 day after therapeutic anti-PD-L1 antibody treatment. In some embodiments, the second time point is used to detect the level of expression of PD-L1 in the subject about 5 days after therapeutic anti-PD-L1 antibody treatment. In specific embodiments, the therapeutic anti-PD-L1 antibody used in the treatment is atezolizumab.

In some embodiments, the second time point is used to measure or detect the level of expression of PD-L1 in the subject after any later or subsequent treatment with a therapeutic anti-PD-L1 antibody (e.g., a first time point can be taken after a first dose of a therapeutic anti-PD-L1 antibody and compared to a sample taken after a second or third dose of the therapeutic anti-PD-L1 antibody). In some embodiments, the second time point is used to measure or detect the level of expression of PD-L1 in the subject about 1 hour after, about 2 hours after, about 3 hours after, about 4 hours after, about 5 hours after, about 6 hours after, about 7 hours after, about 8 hours after, about 9 hours after, about 10 hours after, about 11 hours after, about 12 hours after, about 18 hours after, about 1 day after, about 1.5 days after, about 2 days after, about 2.5 days after, about 3 days after, about 3.5 days after, about 4 days after, about 4.5 days after, about 5 days after, about 5.5 days after, about 6 days after, about 6.5 days after, about 1 week after, about 1.5 weeks after, about 2 weeks after, about 2.5 weeks after, about 3 weeks after, about 3.5 weeks after, about 4 weeks after, about 1 month after, about 1.5 months after, about 2 months after, about 2.5 months after, about 3 months after, about 3.5 months after, about 4 months after, about 4.5 months after, about 5 months after, about 5.5 months after, about 6 months after, about 6.5 months after, about 7 months after, about 7.5 months after, about 8 months after, about 8.5 months after, about 9 months after, about 9.5 months after, about 10 months after, about 10.5 months after, about 11 months after, about 11.5 months after, or about 12 months after any later or subsequent therapeutic anti-PD-L1 antibody treatment. In some embodiments, the second time point is used to measure or detect the level of expression of PD-L1 in the subject about 1 hour after any later or subsequent therapeutic anti-PD-L1 antibody treatment. In some embodiments, the second time point is used to measure or detect the level of expression of PD-L1 in the subject about 4 hours after any later or subsequent therapeutic anti-PD-L1 antibody treatment. In some embodiments, the second time point is used to measure or detect the level of expression of PD-L1 in the subject about 8 hours after any later or subsequent therapeutic anti-PD-L1 antibody treatment. In some embodiments, the second time point is used to measure or detect the level of expression of PD-L1 in the subject about 12 hours after any later or subsequent therapeutic anti-PD-L1 antibody treatment. In some embodiments, the second time point is used to measure or detect the level of expression of PD-L1 in the subject about 18 hours after any later or subsequent therapeutic anti-PD-L1 antibody treatment. In some embodiments, the second time point is used to measure or detect the level of expression of PD-L1 in the subject about 1 day after any later or subsequent therapeutic anti-PD-L1 antibody treatment. In some embodiments, the second time point is used to measure or detect the level of expression of PD-L1 in the subject about 1.5 days after any later or subsequent therapeutic anti-PD-L1 antibody treatment. In some embodiments, the second time point is used to measure or detect the level of expression of PD-L1 in the subject about 2 days after any later or subsequent therapeutic anti-PD-L1 antibody treatment. In some embodiments, the second time point is used to measure or detect the level of expression of PD-L1 in the subject about 2.5 days after any later or subsequent therapeutic anti-PD-L1 antibody treatment. In some embodiments, the second time point is used to measure or detect the level of expression of PD-L1 in the subject about 3 days after any later or subsequent therapeutic anti-PD-L1 antibody treatment. In some embodiments, the second time point is used to measure or detect the level of expression of PD-L1 in the subject about 3.5 days after any later or subsequent therapeutic anti-PD-L1 antibody treatment. In some embodiments, the second time point is used to measure or detect the level of expression of PD-L1 in the subject about 4 days after any later or subsequent therapeutic anti-PD-L1 antibody treatment. In some embodiments, the second time point is used to measure or detect the level of expression of PD-L1 in the subject about 4.5 days after any later or subsequent therapeutic anti-PD-L1 antibody treatment. In some embodiments, the second time point is used to measure or detect the level of expression of PD-L1 in the subject about 5 days after any later or subsequent therapeutic anti-PD-L1 antibody treatment. In specific embodiments, the therapeutic anti-PD-L1 antibody used in the treatment is atezolizumab.

In certain embodiments, changes in the level of expression of PD-L1 between the first time point and the second time point are used to assess the progression of disease in response to the therapeutic anti-PD-L1 antibody therapy. In certain embodiments, changes in the level of expression of PD-L1 between the first time point and the second time point are used to assess disease stability in response to the therapeutic anti-PD-L1 antibody therapy. In certain embodiments, changes in the level of expression of PD-L1 between the first time point and the second time point are used to determine the continued dose of the therapeutic anti-PD-L1 antibody therapy. In certain embodiments, changes in the level of expression of PD-L1 between the first time point and the second time point are used to determine the course of therapy with the therapeutic anti-PD-L1 antibody (e.g., continued dosing, discontinued dosing, dosing in combination with a second or third chemotherapeutic agents, increased dosing, decreased dosing, maintenance dosing, etc.). In specific embodiments, the therapeutic anti-PD-L1 antibody used in the treatment is atezolizumab.

Additional embodiments of a baseline are as follows: in certain embodiments, a baseline refers to samples taken from a subject before treatment with a therapeutic anti-PD-L1 antibody (e.g., atezolizumab); in specific embodiments, the therapeutic anti-PD-L1 antibody used in the treatment is atezolizumab; in specific embodiments, the baseline is a sample taken prior to any treatment with a therapeutic anti-PD-L1 antibody and can be used in comparison with a sample taken after a treatment with a therapeutic anti-PD-L1 antibody (e.g., a baseline can be taken before the first dose of the therapeutic anti-PD-L1 antibody and compared to a sample taken after the first, second, third, fourth, or later dose of the therapeutic anti-PD-L1 antibody); and in specific embodiments, the baseline is a sample taken prior to any given treatment with a therapeutic anti-PD-L1 antibody and can be used in comparison with a sample taken after any later treatment with a therapeutic anti-PD-L1 antibody (e.g., a baseline can be taken after a first dose of the therapeutic anti-PD-L1 antibody and compared to a sample taken after a second or third dose of the therapeutic anti-PD-L1 antibody).

V. Kits

The assay methods of this invention can be provided in the form of a kit. In one embodiment, such a kit comprises an anti-PD-L1 antibody or a composition comprising an anti-PD-L1 antibody as described herein. In some embodiments, such a kit is a packaged combination including the basic elements of: an anti-PD-L1 antibody, and instructions on how to perform the assay method using these reagents. These basic elements are defined hereinabove.

The kit may further comprise a solid support for the anti-PD-L1 antibody, which may be provided as a separate element or on which the anti-PD-L1 antibodies are already immobilized.

The kit may also contain other additives such as stabilizers, washing and incubation buffers, and the like.

The components of the kit may be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

EXAMPLES

The following examples are included for illustrative purposes only and are not intended to limit the scope of the invention.

Example 1: Evaluation of Anti-PD-L1 Antibody Clone 14D3 Characteristics

Clone 14D3 is a specific, non-competing clone to the monoclonal anti-PD-L1 antibody known as Atezolizumab.

14D3 is a mouse antibody with an IgG1 isotype and a kappa light chain. The immunogen for generating 14D3 was the MOLM-1 megakaryocytic cell line and is cross-reactive with human PD-L1 as well as Cynomolgus PD-L1. The competing and non-competing characteristics of antibody 14D3, an anti-human PD-L1 antibody, were evaluated against commercially available anti-human PD-L1 antibodies.

Methods

Antibodies

PD-L1 binding characteristics of two commercially available anti-human PD-L1 antibodies were compared to PD-L1 binding characteristics of anti-PDL-1 14D3 antibody. Two versions of the 14D3 antibody were used in the comparison studies, one version labeled with phycoerythrin (PE), referred to herein as anti-PD-L1 PE 14D3, and the other version labeled with Alexa Fluor 647® (AF647), referred to herein as anti-PD-L1 AF647 14D3. Commercial antibodies were anti-PD-L1 antibody clone 29E.23 labeled with PE (Biolegend), referred to herein as anti-PD-L1 PE 29E.23 and anti-PD-L1 antibody clone 29E.23 labeled with Allophycocyanin (APC) (Biolegend), referred to herein as anti-PD-L1 APC 29E.23.

Blood Stimulation

About 4 mL to 5 mL of whole blood was obtained from healthy human subjects and placed in a vacutainer tube with sodium heparin as an anticoagulant. Two 15 mL conical tubes were prepared and labeled as follows: 1) Blood with no stimulation; and 2) Blood with stimulation. Each tube was filled with 3 mL of healthy blood. According to Miltenyi Biotec, it is recommended to use 20 uL per each mL of whole blood. Therefore, 60 µl of phosphate buffered saline (PBS) was added to Tube 1, our non-stimulated tube, and 60 µl of CytoStim® (Miltenyi Biotec) was added to Tube 2, which contained 3 mL of whole blood. The caps on the tubes were loosely secured to allow oxygen and $CO_2$ to flow in and out of the tubes. The tubes were placed in a $CO_2$ incubator for 24 hours at 37° C.

Blocking with Atezolizumab

Four sets of five 5 mL-round bottom test tubes were prepared and grouped as follows: 1) Stimulation and No Drug; 2) Stimulation+ Drug; 3) No stimulation and No Drug; and 4) No stimulation+ Drug. Once the blood samples had been incubated for 24 hours during the stimulation step, 100 µL of stimulated blood was added to each test tube in Group 1 and Group 2 while 100 µL of unstimulated blood was added to each test tube in Group 3 and Group 4.

Atezolizumab served as the drug for the blocking portion of the assay. For preparation of the drug, 2 µL of Atezolizumab at a concentration of 100 µg/mL was added to 18 µL of PBS for a 1:10 dilution. For test tubes that were labeled as "+ Drug" (i.e., Group 2 and Group 4), 1.6 µl of the diluted Atezolizumab was added to each test tube. Test tubes labeled as "No Drug" (i.e., Group 1 and Group 3) received 1.6 µL of PBS. The test tubes were mixed well by vortexing and were then incubated at room temperature for 30 minutes in the dark.

Surface Marker Stain

Five surface marker cocktails were prepared (Table 2).

TABLE 2

Surface Marker Cocktails

| Cocktail Tube | AF488/ FITC | PE | PerCP | PE-Cy7 | AF647/ APC | BV421 | BV510 | BD Horizon Brilliant Stain Buffer (BD Biosciences) |
|---|---|---|---|---|---|---|---|---|
| 1 | CD8 (20 µL) | PD-L1 Biolegend 5 µL | CD45 (10 µL) | CD4 (5 µL) | | CD19 (2 µL) | CD33 (5 µL) | 50 µL |
| 2 | CD8 (20 µL) | | CD45 (10 µL) | CD4 (5 µL) | PD-L1 Biolegend 5 µL | CD19 (2 µL) | CD33 (5 µL) | 50 µL |
| 3 | CD8 (20 µL) | PD-L1 GNE 0.5 µL | CD45 (10 µL) | CD4 (5 µL) | | CD19 (2 µL) | CD33 (5 µL) | 50 µL |
| 4 | CD8 (20 µL) | | CD45 (10 µL) | CD4 (5 µL) | PD-L1 GNE 0.5 µL | CD19 (2 µL) | CD33 (5 µL) | 50 µL |
| 5 Ctrl | CD8 (20 µL) | | CD45 (10 µL) | CD4 (5 µL) | | CD19 (2 µL) | CD33 (5 µL) | 50 µL |

After incubation with the drug (i.e., Atezolizumab) or with PBS, a cocktail of surface markers was added to each test tube containing blood with or without the anti-PD-L1, and with or without stimulation (Table 2). After adding the indicated amount of cocktail, the indicated amount of PBS was added to bring the total cocktail volume to 100 µL (Table 3). The test tubes were then incubated for 30 minutes at room temperature in the dark.

TABLE 3

Surface staining of four test groups

| | Group 1 (Stimulation and No Drug) | Group 2 (Stimulation + Drug) | Group 3 (No stimulation and No Drug) | Group 4 (No stimulation + Drug) |
|---|---|---|---|---|
| Test Tube 1 | Cocktail tube 1 (97 µL) PBS (3 µL) | Cocktail tube 1 (97 µL) PBS (3 µL) | Cocktail tube 1 (97 µL) PBS (3 µL) | Cocktail tube 1 (97 µL) PBS (3 µL) |

TABLE 3-continued

| | Surface staining of four test groups | | | |
|---|---|---|---|---|
| | Group 1 (Stimulation and No Drug) | Group 2 (Stimulation + Drug) | Group 3 (No stimulation and No Drug) | Group 4 (No stimulation + Drug) |
| Test Tube 2 | Cocktail tube 2 (97 µL) PBS (3 µL) | Cocktail tube 2 (97 µL) PBS (3 µL) | Cocktail tube 2 (97 µL) PBS (3 µL) | Cocktail tube 2 (97 µL) PBS (3 µL) |
| Test Tube 3 | Cocktail tube 3 (92.5 µL) PBS (7.5 µL) | Cocktail tube 3 (92.5 µL) PBS (7.5 µL) | Cocktail tube 3 (92.5 µL) PBS (7.5 µL) | Cocktail tube 3 (92.5 µL) PBS (7.5 µL) |
| Test Tube 4 | Cocktail tube 4 (92.5 µL) PBS (7.5 µL) | Cocktail tube 4 (92.5 µL) PBS (7.5 µL) | Cocktail tube 4 (92.5 µL) PBS (7.5 µL) | Cocktail tube 4 (92.5 µL) PBS (7.5 µL) |
| Test Tube 5 | Cocktail tube 5 (92 µL) PBS (7 µL) | Cocktail tube 5 (92 µL) PBS (7 µL) | Cocktail tube 5 (92 µL) PBS (7 µL) | Cocktail tube 5 (92 µL) PBS (7 µL) |

Staining for Live or Dead Cells

A Live Dead Kit (Invitrogen) was brought to room temperature. The kit included a near-IR fluorescent reactive dye and DMSO. 1× Pharm Lyse was made by mixing 10 mL of 10× Pharm Lyse (BD Biosciences) in 90 mL distilled water. After surface staining the cells in the test tubes, the tubes were vortexed and 3 mL of 1× Pharm Lyse was added to each test tube. The test tubes were vortexed again to enhance lysis of the cells in the presence of Pharm Lyse. The test tubes were then incubated for 15 minutes at room temperature in the dark. Following incubation, the test tubes were centrifuged for 5 minutes at 300 RCF/1500 to 1600 RPM. After centrifugation, the supernatant was aspirated as much as possible without disturbing the cell pellet. The bottom of each test tube was then flicked to break the cell pellet before washing the cells in 3 mL phosphate-buffered saline (PBS). The test tubes were centrifuged once more for 5 minutes at 300 RCF/1500 to 1600 RPM. The supernatant was then aspirated as before without disturbing the cell pellet. The bottom of each test tube was flicked to break the cell pellet and 1 mL of PBS was added to each test tube. A test tube was selected to perform a cell count using the BioRad TC20 cell counter. If the cell count was above 2 million live cells per mL of PBS in the tube, the concentration was adjusted to be 1 million live cells per mL and diluted accordingly using PBS. The Live/Dead dye from the kit was prepared by adding 50 µL of DMSO to the Near-IR fluorescent reactive dye tube followed by mixing. An amount of 1 µL of Live-Dead dye was added to each test tube and mixed well. The test tubes were incubated for 30 minutes at room temperature in the dark. After incubation, the cells were washed in 2 mL BD Pharmigen FBS followed by centrifugation for 5 minutes at 300 RCF/1500 to 1600 RPM. The supernatant was aspirates as much as possible without disturbing cell pellet. A solution of 1% paraformaldehyde was prepared by adding 3 mL of 16% paraformaldehyde to 45 mL PBS. The bottom of each test tube was flicked to break the cell pellet and 250 µL of 1% paraformaldehyde was added to each test tube before the test tubes were vortexed. The signal was acquired from the test tube samples on BD FACSCanto™ II (BD Biosciences) within 4 hours of finishing preparation.

Compensation controls were created (Table 4). To create the compensation controls, nine 5 mL round bottom tubes were created to contain the following: 1) Control Tube-No Stain; 2) AF488/FITC; 3) PE; 4) PerCP; 5) PE-Cy7; 6) AF647/APC; 7) BV421; 8) BV510; and 9) APC-H7. One drop of UltraComp eBeads (Invitrogen) was added to each tube. The indicated antibodies were added at the indicated volume (Table 3). The compensation controls were incubated for 15-20 minutes at room temperature in the dark. The tubes were then washed in 3 mL BD FBS before centrifugation for 5 minutes at 300 RCF/1500 to 1600 RPM. The supernatant was aspirated as much as possible without disturbing the beads pellet. An amount of 100 µL of BD FBS was added to each compensation control tube in preparation to be acquired on BD FACSCanto™ II.

TABLE 4

| | Compensation Controls for each surface marker cocktail | | | | | | | |
|---|---|---|---|---|---|---|---|---|
| | Control Tube | AF488/ FITC | PE | PERCP | PE-CY7 | AF647/ APC | BV421 | BV510 | APC-H7 |
| Compensation Control Antibodies | Blank (only 1 drop of beads with no antibody) | CD8 FITC (20 µL) | CD4 PE (20 µL) | CD45 (10 µL) | CD4 (5 µL) | CD4 APC (20 µL) | CD19 BV421 (2.5 µL) | CD33 (2.5 µL) | CD4 APC-H7 (5 µL) |

Results

Figure 3A:
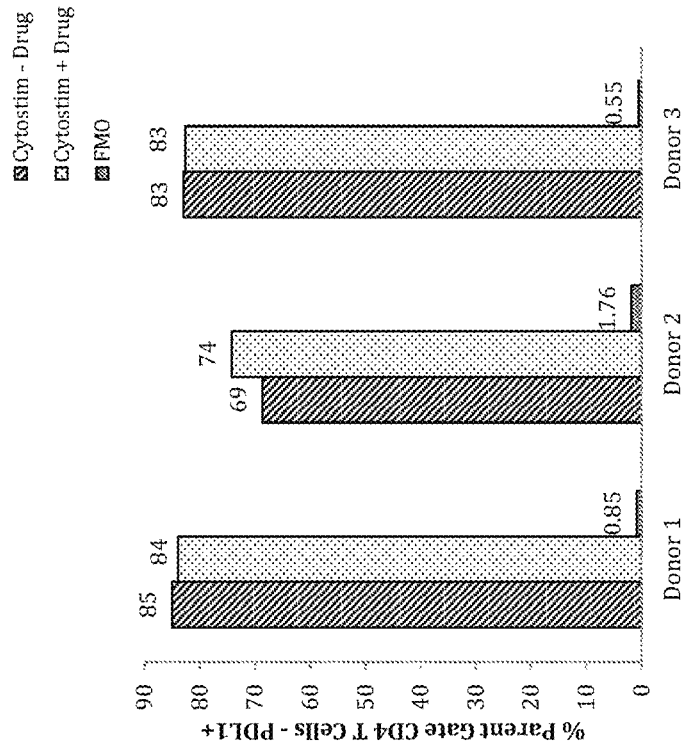
FIGS. 3A and 3B is a graph showing the percentage (%) of PD-L1+CD4+ T cells in blood obtained from healthy human donors and A) stained with anti-PD-L1 PE 29E.23 in the absence of Atezolizumab (− Drug) or in the presence of Atezolizumab (+ Drug) after stimulation with CytoStim®; or B) stained with anti-PD-L1 PE 14.D3 in the absence of Atczolizumab (− Drug) or in the presence of Atezolizumab (+ Drug) after stimulation with CytoStim®. FMO indicates fluorescence minus one negative gating control.
Figure 4B:
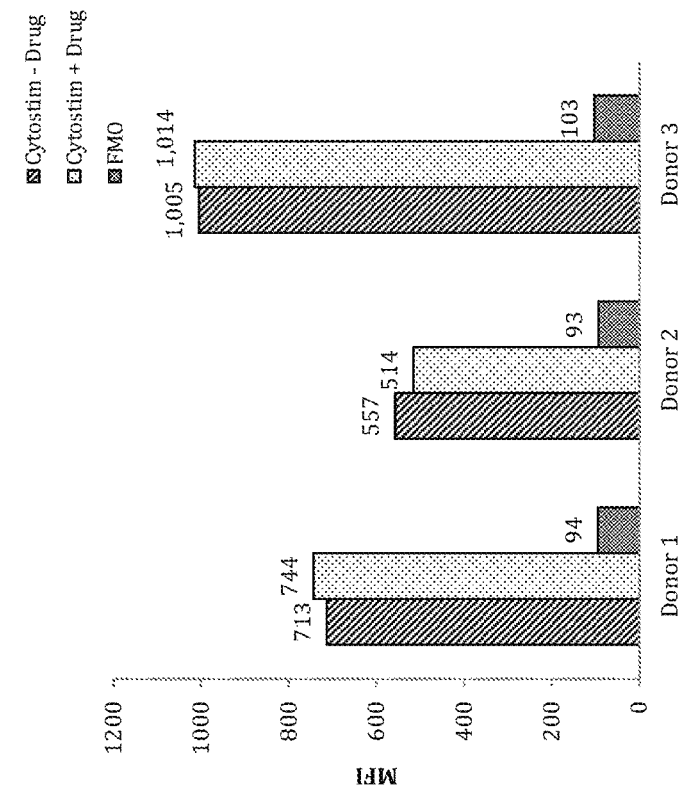
FIGS. 4A and 4B is a graph showing the median fluorescent intensity (MFI) of PD-L1+CD8+ T cells in blood obtained from healthy human donors and A) stained with anti-PD-L1 PE 29E.23 in the absence of Atezolizumab (− Drug) or in the presence of Atezolizumab (+ Drug) after stimulation with CytoStim®; or B) stained with anti-PD-L1 PE 14.D3 in the absence of Atezolizumab (− Drug) or in the presence of Atezolizumab (+ Drug) after stimulation with CytoStim®. FMO indicates fluorescence minus one negative gating control.
Figure 4A:
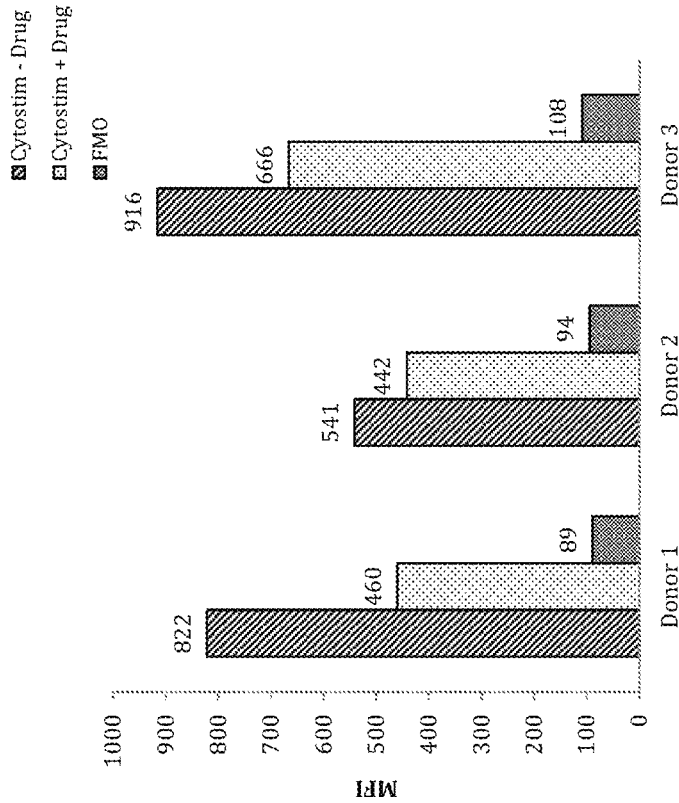
Figure 5A:
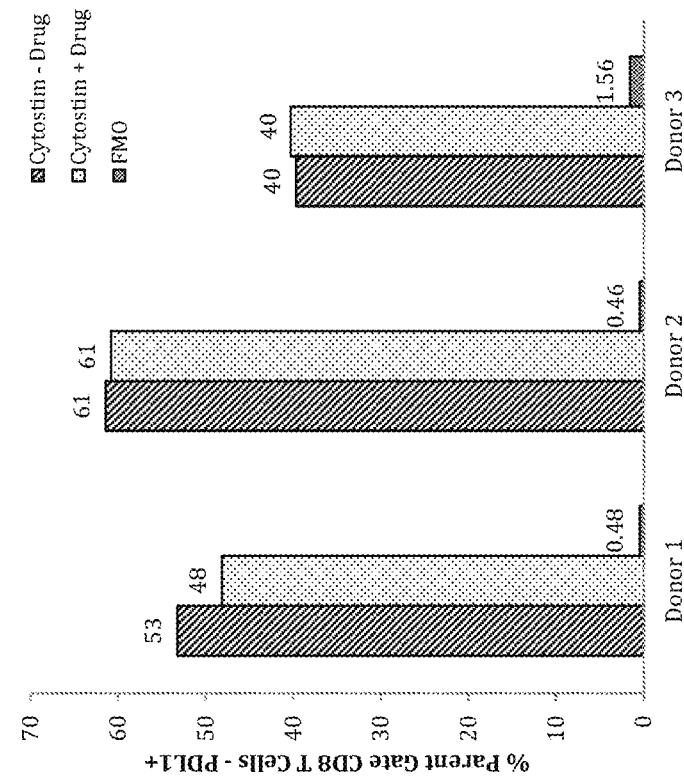
FIGS. 5A and 5B is a graph showing the percentage (%) of PD-L1+CD8+ T cells in blood obtained from healthy human donors and A) stained with anti-PD-L1 PE 29E.23 in the absence of Atezolizumab (− Drug) or in the presence of Atezolizumab (+ Drug) after stimulation with CytoStim®; or B) stained with anti-PD-L1 PE 14.D3 in the absence of Atezolizumab (− Drug) or in the presence of Atezolizumab (+ Drug) after stimulation with CytoStim®. FMO indicates fluorescence minus one negative gating control.
Figure 6A:
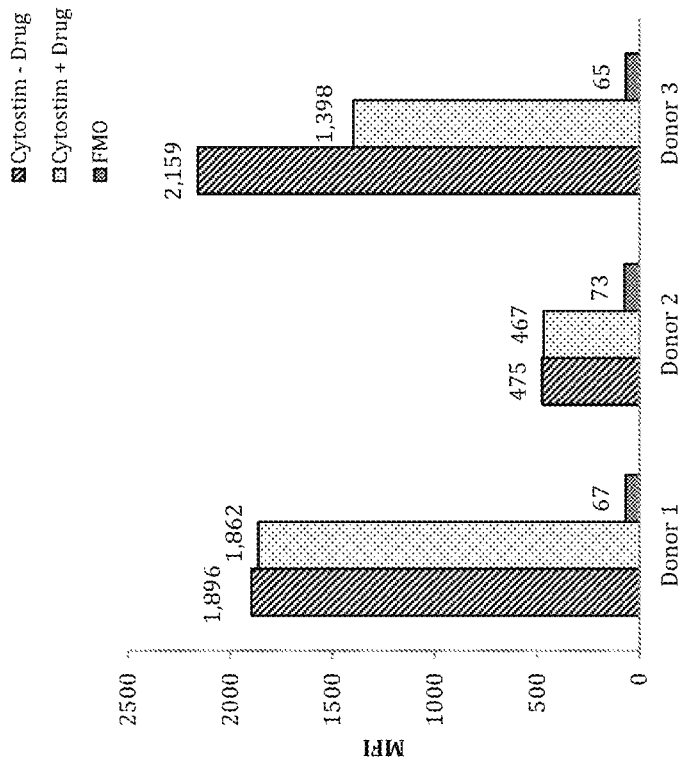
FIGS. 6A and 6B is a graph showing the median fluorescent intensity (MFI) of PD-L1+CD19 B cells in blood obtained from healthy human donors and A) stained with anti-PD-L1 PE 29E.23 in the absence of Atezolizumab (− Drug) or in the presence of Atezolizumab (+ Drug) after stimulation with CytoStim®; or B) stained with anti-PD-L1 PE 14.D3 in the absence of Atezolizumab (− Drug) or in the presence of Atezolizumab (+ Drug) after stimulation with CytoStim®. FMO indicates fluorescence minus one negative gating control.
Figure 7A:
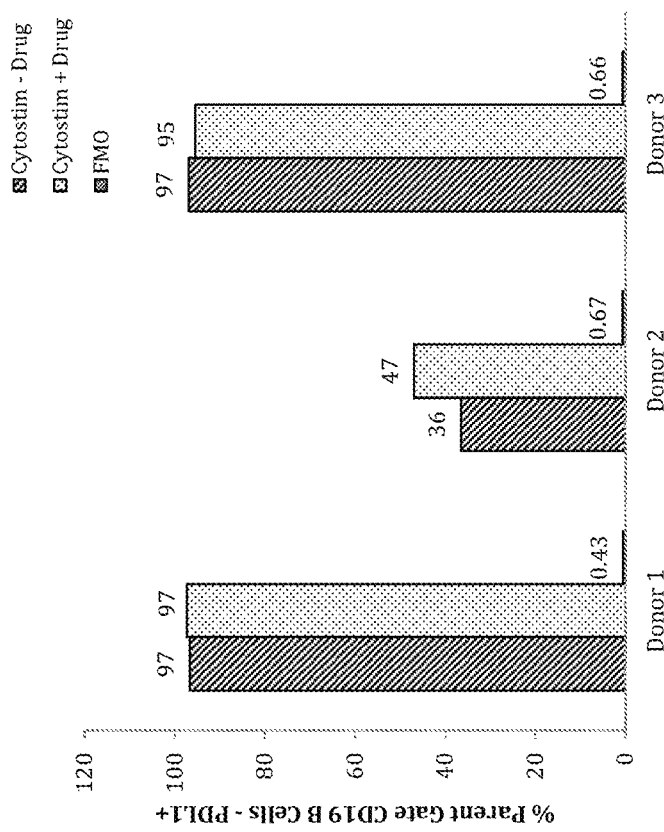
FIGS. 7A and 7B is a graph showing the percentage (%) of PD-L1+CD19 B cells in blood obtained from healthy human donors and A) stained with anti-PD-L1 PE 29E.23 in the absence of Atezolizumab (− Drug) or in the presence of Atezolizumab (+ Drug) after stimulation with CytoStimR; or B) stained with anti-PD-L1 PE 14.D3 in the absence of Atezolizumab (− Drug) or in the presence of Atezolizumab (+ Drug) after stimulation with CytoStim®. FMO indicates fluorescence minus one negative gating control.
Figure 8A:
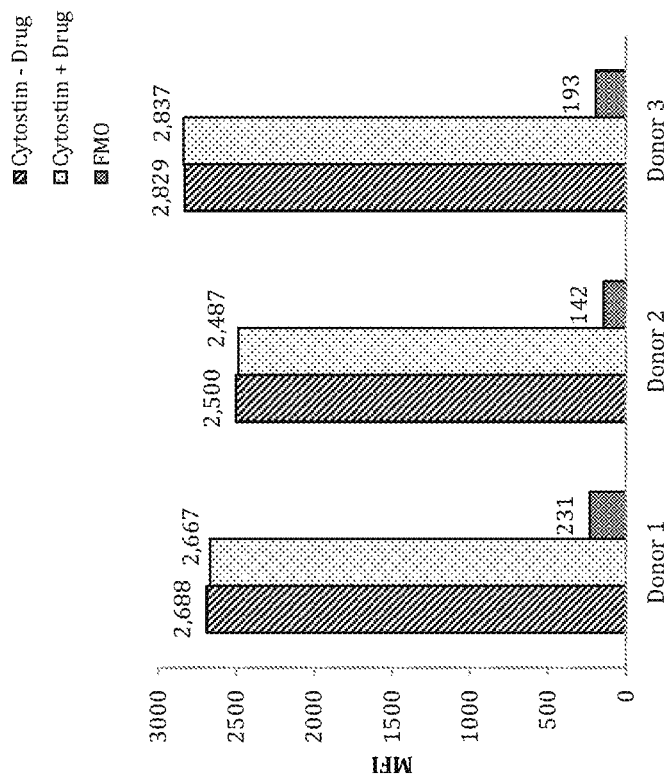
FIGS. 8A and 8B is a graph showing the median fluorescent intensity (MFI) of PD-L1+CD4+ T cells in blood obtained from human healthy donors and A) stained with anti-PD-L1 APC 29E.23 in the absence of Atezolizumab (− Drug) or in the presence of Atezolizumab (+ Drug) after stimulation with CytoStim®; or B) stained with anti-PD-L1 AF647 14.D3 in the absence of Atezolizumab (− Drug) or in the presence of Atezolizumab (+ Drug) after stimulation with CytoStim®. FMO indicates fluorescence minus one negative gating control.
Figure 9A:
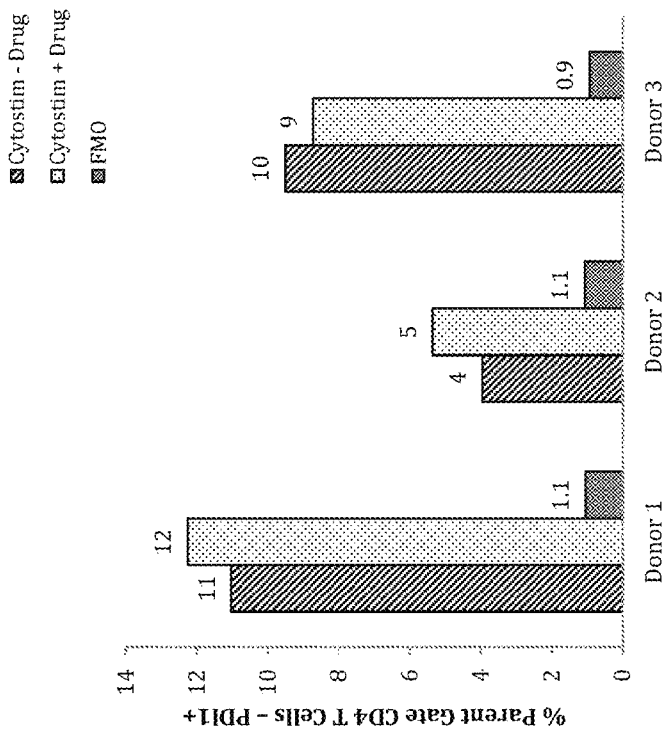
FIGS. 9A and 9B is a graph showing the percentage (%) of PD-L1+CD4+ T cells in blood obtained from human healthy donors and A) stained with anti-PD-L1 APC 29E.23 in the absence of Atezolizumab (− Drug) or in the presence of Atezolizumab (+ Drug) after stimulation with CytoStim®; or B) stained with anti-PD-L1 AF647 14.D3 in the absence of Atczolizumab (− Drug) or in the presence of Atezolizumab (+ Drug) after stimulation with CytoStim®. FMO indicates fluorescence minus one negative gating control.
Figure 10A:
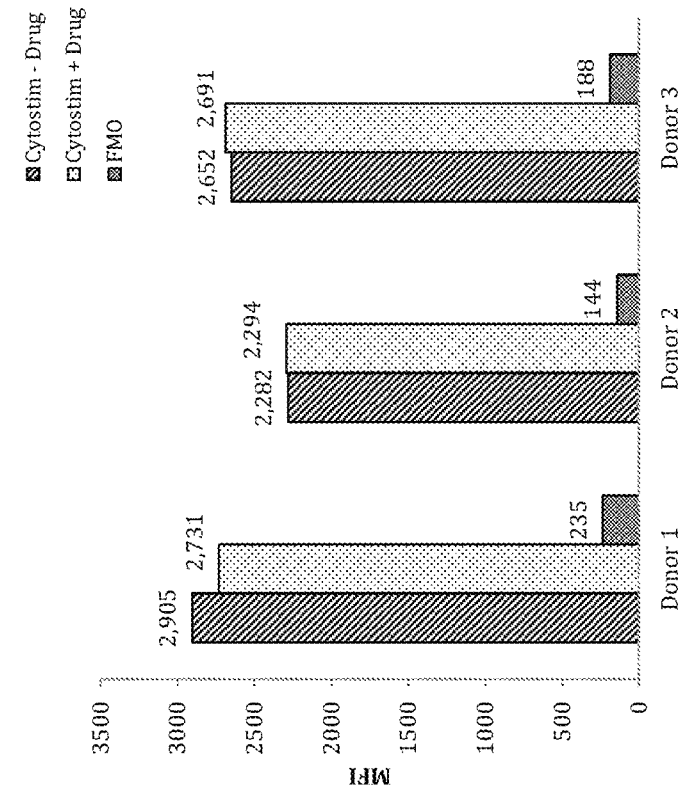
FIGS. 10A and 10B is a graph showing the median fluorescent intensity (MFI) of PD-L1+CD8+ T cells in blood obtained from human healthy donors and A) stained with anti-PD-L1 APC 29E.23 in the absence of Atezolizumab (− Drug) or in the presence of Atezolizumab (+ Drug) after stimulation with CytoStim®; or B) stained with anti-PD-L1 AF647 14.D3 in the absence of Atezolizumab (− Drug) or in the presence of Atezolizumab (+ Drug) after stimulation with CytoStim®. FMO indicates fluorescence minus one negative gating control.
Figure 11A:
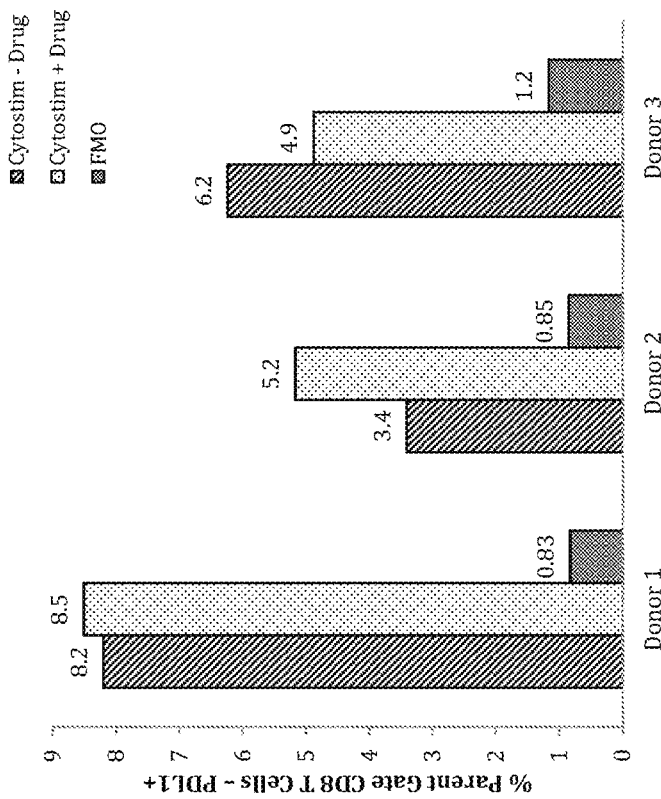
FIGS. 11A and 11B is a graph showing the percentage (%) of PD-L1+CD8+ T cells in blood obtained from human healthy donors and A) stained with anti-PD-L1 APC 29E.23 in the absence of Atezolizumab (− Drug) or in the presence of Atezolizumab (+ Drug) after stimulation with CytoStimt; or B) stained with anti-PD-L1 AF647 14.D3 in the absence of Atezolizumab (− Drug) or in the presence of Atezolizumab (+ Drug) after stimulation with CytoStim®. FMO indicates fluorescence minus one negative gating control.
Figure 12A:
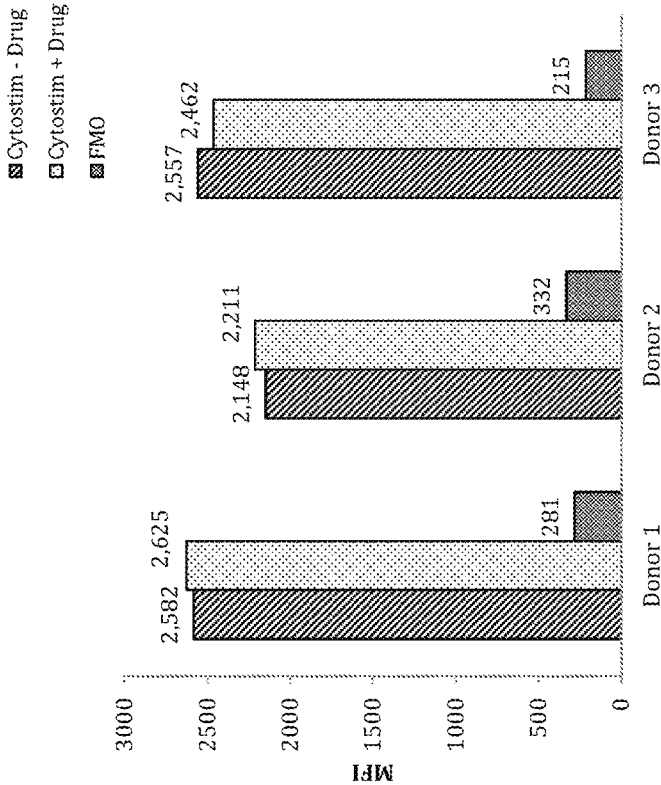
FIGS. 12A and 12B is a graph showing the median fluorescent intensity (MFI) of PD-L1+CD19 B cells in blood obtained from human healthy donors and A) stained with anti-PD-L1 APC 29E.23 in the absence of Atezolizumab (− Drug) or in the presence of Atezolizumab (+ Drug) after stimulation with CytoStim®; or B) stained with anti-PD-L1 AF647 14.D3 in the absence of Atezolizumab (− Drug) or in the presence of Atezolizumab (+ Drug) after stimulation with CytoStim®. FMO indicates fluorescence minus one negative gating control.
Figure 13A:
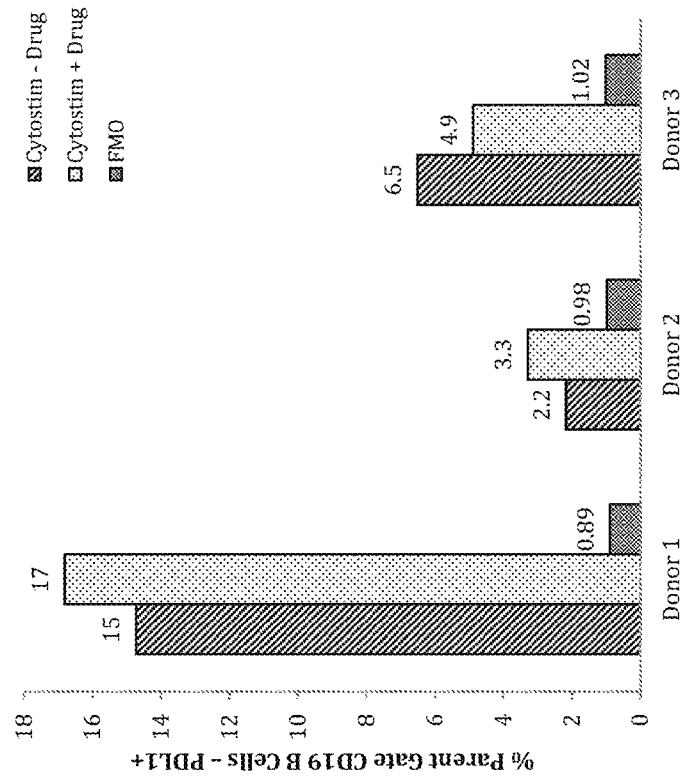
FIGS. 13A and 13B is a graph showing the percentage (%) of PD-L1+CD19 B cells in blood obtained from human healthy donors and A) stained with anti-PD-L1 APC 29E.23 in the absence of Atezolizumab (− Drug) or in the presence of Atezolizumab (+ Drug) after stimulation with CytoStim®; or B) stained with anti-PD-L1 AF647 14.D3 in the absence of Atezolizumab (− Drug) or in the presence of Atezolizumab (+ Drug) after stimulation with CytoStim®. FMO indicates fluorescence minus one negative gating control.

It was observed that when Atezolizumab was present, the level of PD-L1 surface expression detection decreased in cells stained with the commercial anti-PD-L1 PE 29E.23 antibody. Specifically, binding analysis by flow cytometry determined that the commercial anti-PD-L1 PE 29E.23 antibody competed with Atezolizumab for binding to PD-L1 expressed by CD4+ T cells (FIG. 2A and FIG. 3A), CD8+ T cells (FIG. 4A and FIG. 5A) and CD19 B cells (FIG. 6A and FIG. 7A) in stimulated blood from healthy donors. Similar binding results were observed in assays utilizing the commercial anti-PD-L1 APC 29E.23 antibody in CD4+ T cells (FIG. 8A and FIG. 9A), CD8+ T cells (FIG. 10A and FIG. 11A) and CD19 B cells (FIG. 12A and FIG. 13A).

Figure 2B:
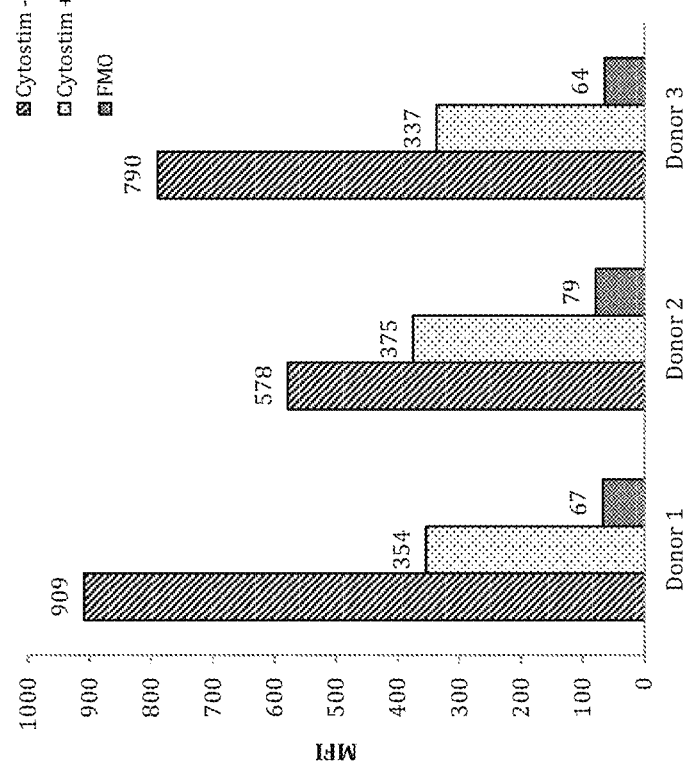
Figure 3B:
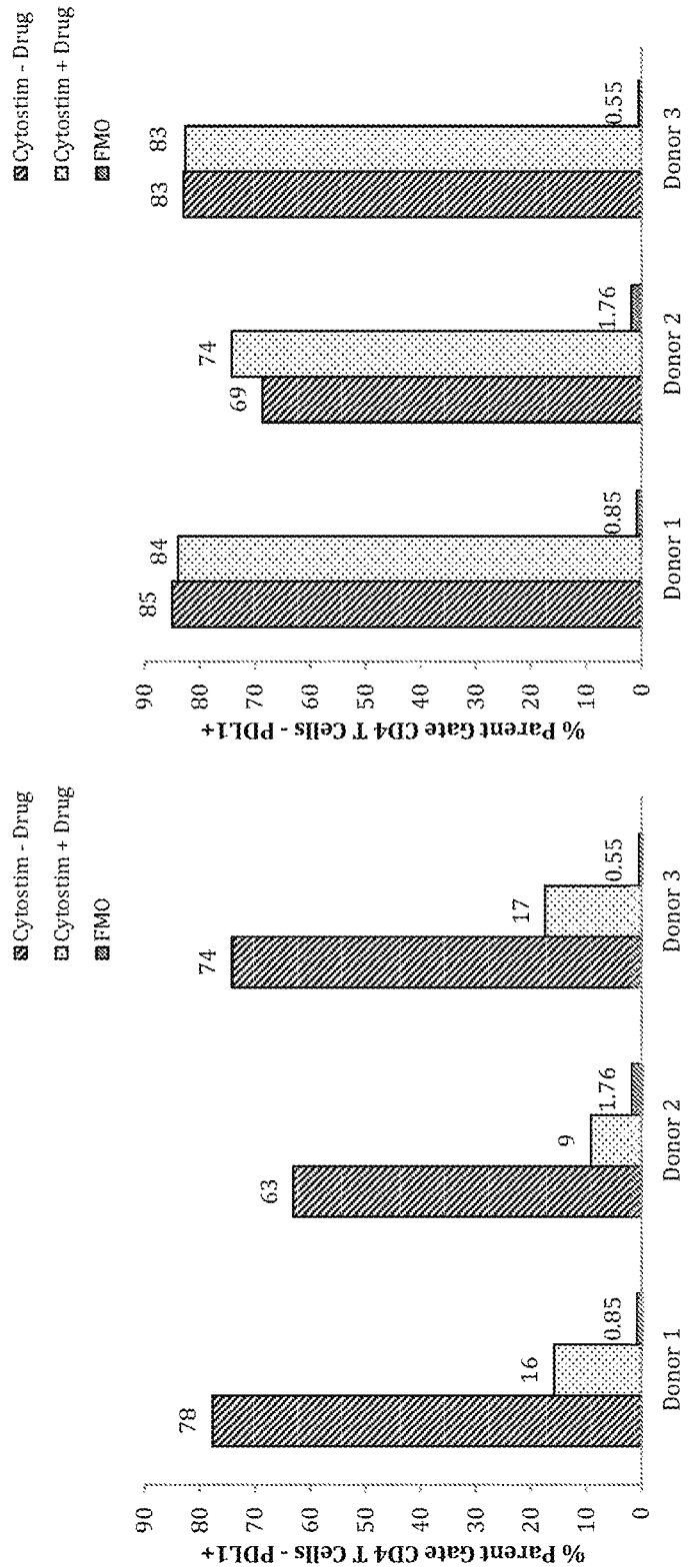
Figure 5B:
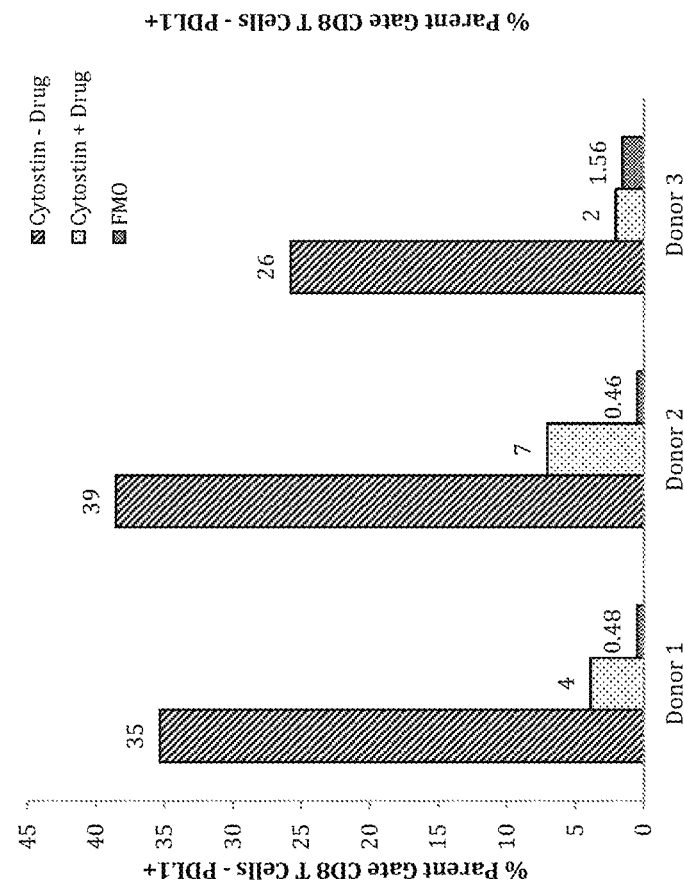
Figure 6B:
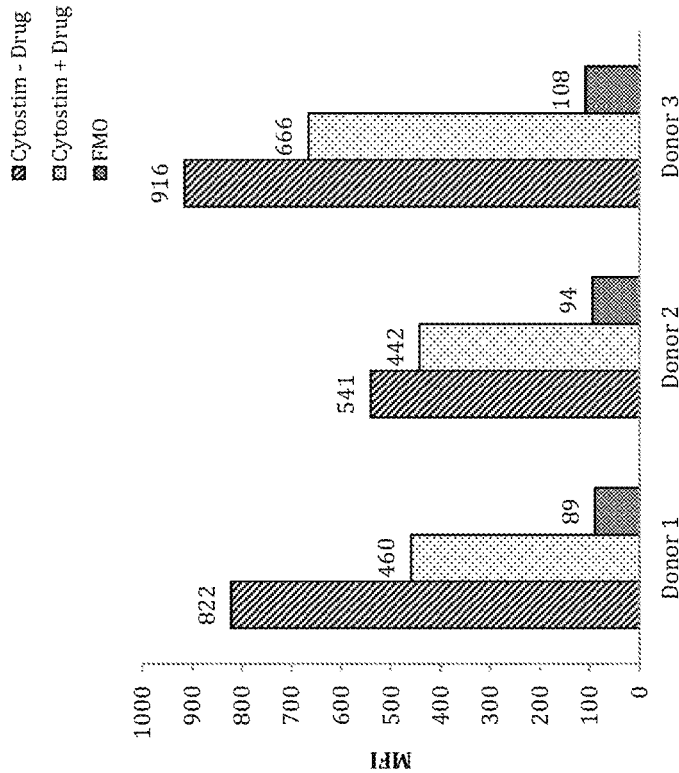
Figure 7B:
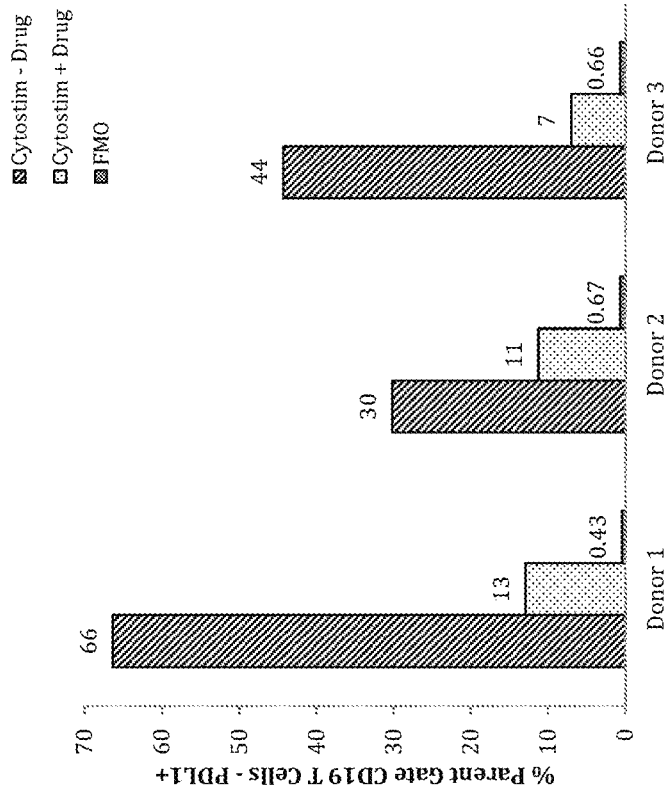
Figure 8B:
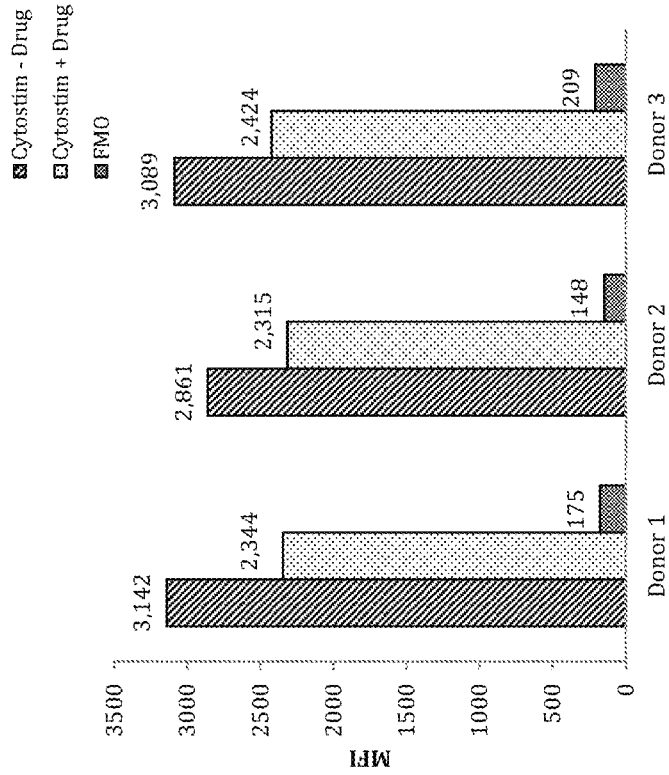
Figure 9B:
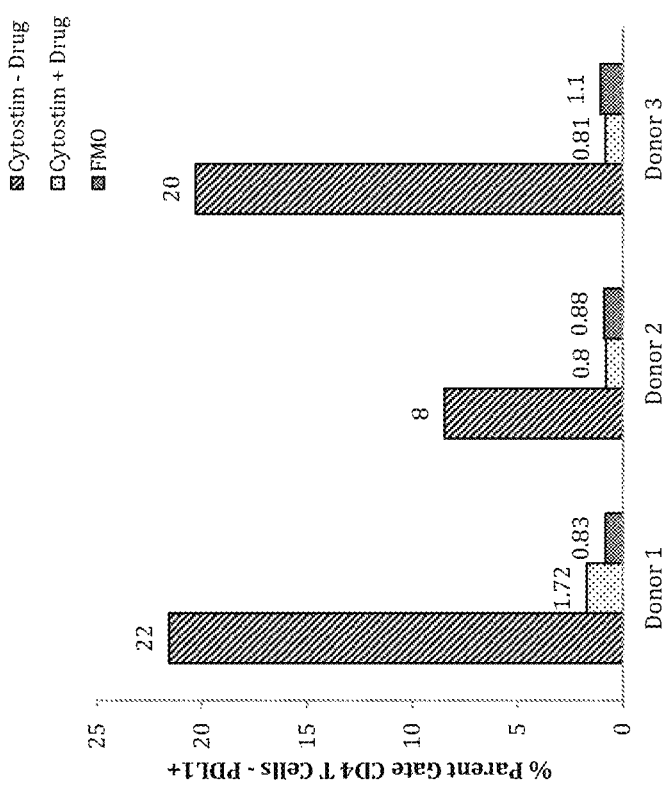
Figure 10B:
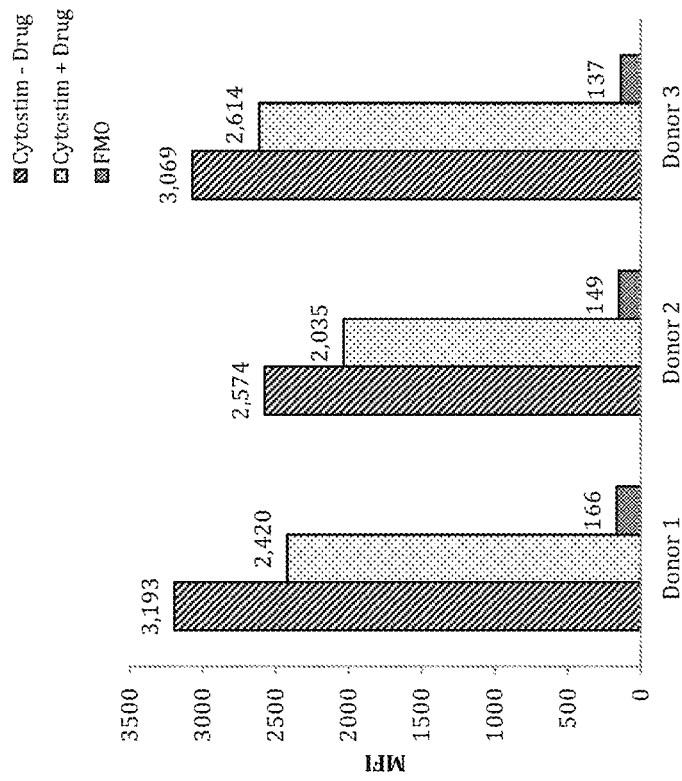
Figure 11B:
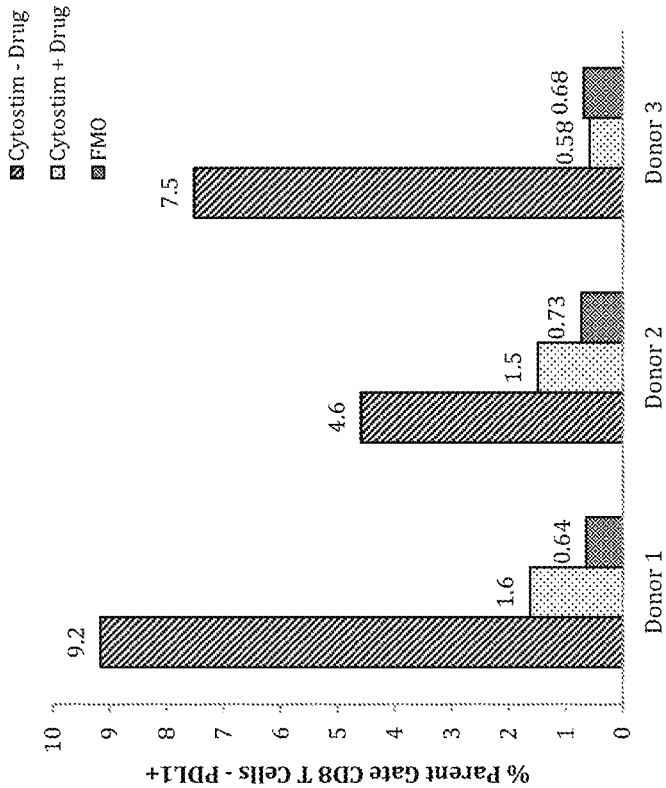
Figure 12B:
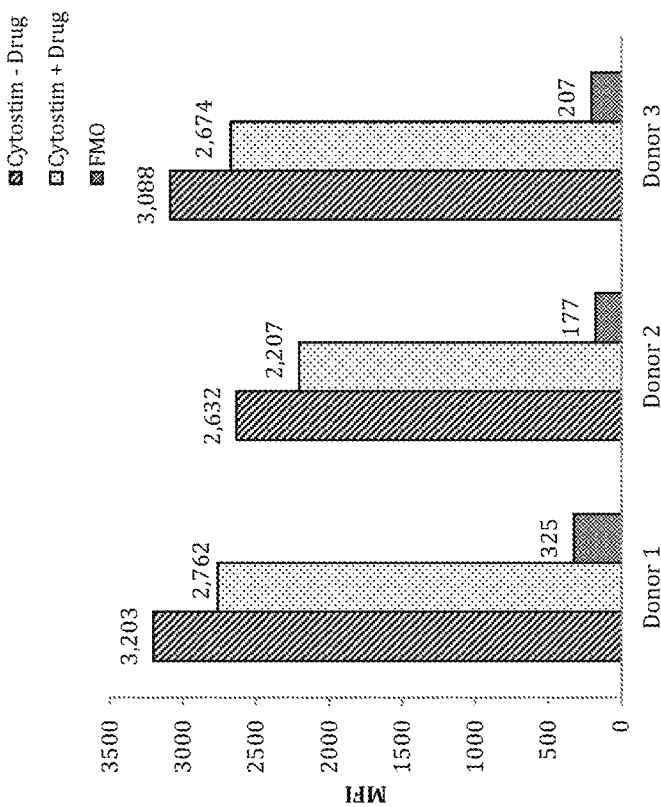
Figure 13B:
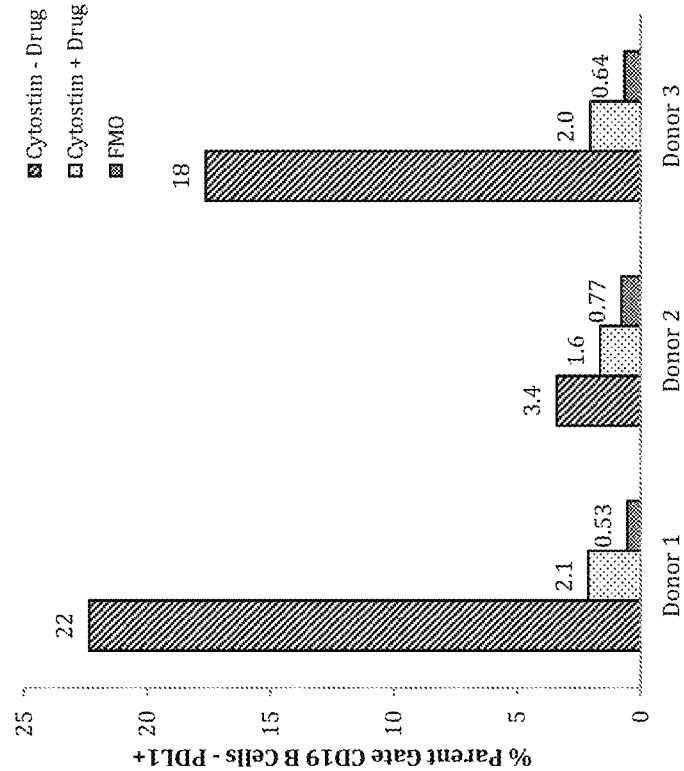

In contrast, the anti-PD-L1 PE 14D3 antibody did not compete with Atezolizumab for binding to PD-L1 expressed by CD4+ T cells (FIG. 2B and FIG. 3B), CD8+ T cells (FIG. 4B and FIG. 5B) and CD19 B cells (FIG. 6B and FIG. 7B) in stimulated blood from healthy donors. These results also extended to the anti-PD-L1 14D3 antibody labeled with AF647 (i.e., anti-PD-L1 AF647 14D3 antibody) in CD4+ T cells (FIG. 8B and FIG. 9B), CD8+ T cells (FIG. 10B and FIG. 11B) and CD19 B cells (FIG. 12B and FIG. 13B).

Figure 15A:
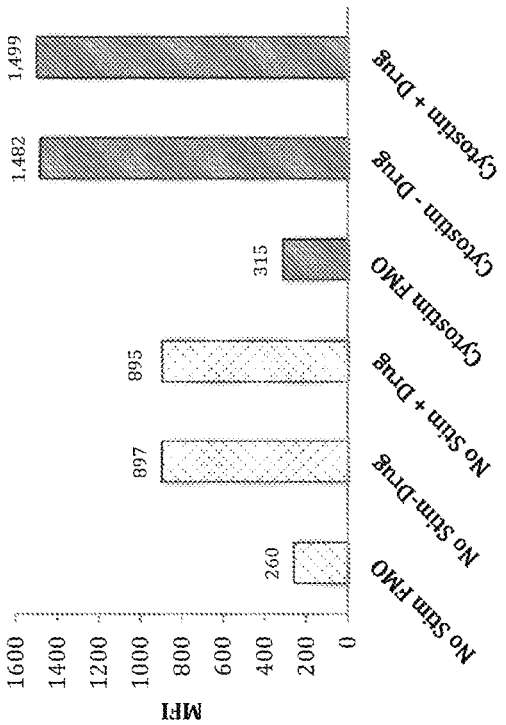
FIG. 15A-C is a graph showing the median fluorescent intensity (MFI) of A) CD4+ T cells, B) CD8+ T cells and C) CD19 B cells in both unstimulated and stimulated blood obtained from healthy donors and stained with anti-PD-L1 AF647 14.D3 antibody in the absence of Atezolizumab (− Drug) or in the presence of Atezolizumab (+ Drug). FMO indicates fluorescence minus one negative gating control. Cytostim indicates CytoStim® stimulation agent. No Stim FMO: anti-PD-L1 AF647 14.D3 antibody not present; No Stim − Drug: anti-PD-L1 AF647 14.D3 antibody was present; No Stim+ Drug: anti-PD-L1 AF647 14.D3 antibody and Atezolizumab were present; Cytostim FMO: anti-PD-L1 AF647 14.D3 antibody not present; Cytostim−Drug: anti-PD-L1 AF647 14.D3 antibody was present; and Cytostim+ Drug: anti-PD-L1 AF647 14.D3 antibody and Atezolizumab were present.
Figure 15B:
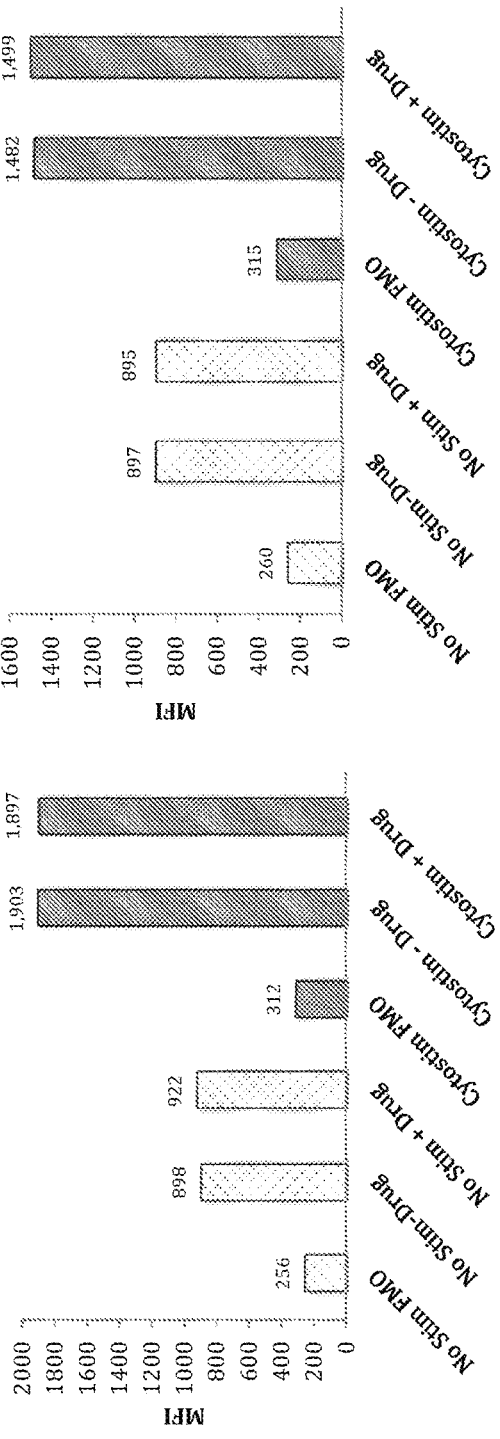
Figure 15C:
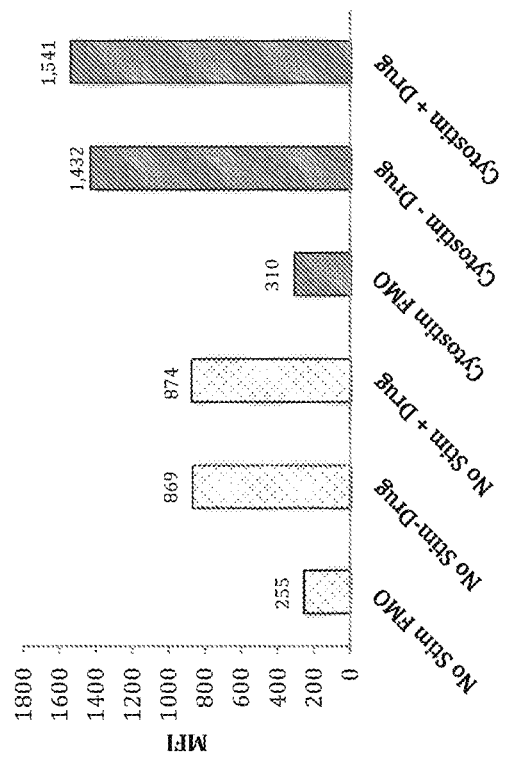

The ability of anti-PD-L1 14D3 antibody labeled with PE (FIG. 14) or AF647 (FIG. 15) to bind PD-L1 on CD4+ T cells, CD8+ T cells, and CD19 B cells in the presence of Atezolizumab is observed in stimulated healthy blood when compared to binding in unstimulated healthy blood. Competition between anti-PD-L1 29E.23 antibody labeled with APC (FIG. 16) and Atezolizumab for binding to PD-L1 on CD4+ T cells, CD8+ T cells, and CD19 B cells can be seen in stimulated healthy blood when compared to binding in unstimulated healthy blood.

Conclusion

These results show that the 14D3 antibody does not compete with Atezolizumab, even at levels expected to be the saturating concentration for Atezolizumab. It was determined that PD-L1 expression on the surface of immune and tumor cells (e.g., live immune and tumor cells) could be quantified using labeled 14D3 antibody in detection assays, such as by a flow cytometry assay, even in the presence of Atezolizumab. However, other commercially available antibodies, such as PD-L1 clone 29E.23 did compete with Atezolizumab which prevents their use as optimal reagents for quantification of PD-L1 expression in immune and tumor cells.

Example 2: Evaluation of PD-L1 Expression in Multiple Myeloma Using Anti-PD-L1 14D3 Antibody 14D3 was assessed for its ability to detect PD-L1 expression in patients with hematological malignancies, in particular, multiple myeloma.

Methods

Fresh bone marrow and fresh whole blood was collected from patients with multiple myeloma (MM). Samples were also collected from healthy subjects. The bone marrow and whole blood was heparinized and stained for surface markers including anti-PD-L1 14D3 antibody as described in Example 1.

Results

Figure 17:
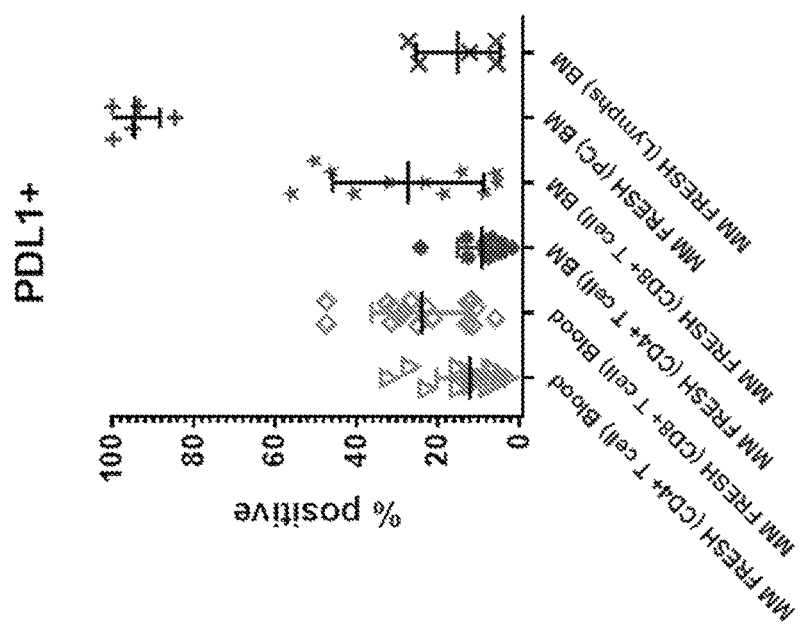
FIG. 17 is a graph showing the expression of PD-L1 in multiple myeloma (MM) in heparinized bone marrow and whole blood stained with anti-PDL-1 14D3 antibody as measured by flow cytometry. PC indicates plasma cell. BM indicates bone marrow. Specific cell populations are identified in parenthesis. Open symbols denote same patient.

Anti-PD-L1 14D3 antibody was able to detect the presence of PD-L1 in bone marrow and whole blood collected from patients with multiple myeloma who have not been treated with a PD-1 check-point inhibitor (FIG. 17).

Conclusion

The 14D3 antibody can be used in the baseline detection of PD-L1 expressed by immune cells circulating peripheral blood as well as by malignant cells from blood and bone marrow of patients diagnosed with hematological malignancies, such as multiple myeloma.

Example 3: Evaluation of PD-L1 Expression in Acute Myeloid Leukemia and Myelodysplastic Syndrome Using Anti-PD-L1 14D3 Antibody 14D3 is assessed for its ability to detect PD-L1 expression in patients with hematological malignancies, in particular acute myeloid leukemia (AML) or myelodysplastic syndrome (MDS).

Methods

Fresh bone marrow and fresh whole blood is collected from patients with acute myeloid leukemia (AML) or myelodysplastic syndrome (MDS). Samples are also collected from healthy subjects. The bone marrow and whole blood is heparinized and stained for surface markers including anti-PD-L1 14D3 antibody as described in Example 1.

Example 4: Evaluation of PD-L1 Expression in Subjects Having Hematological Malignancies and Treated with Atezolizumab Since the 14D3 antibody is non-competing to the epitope of Atezolizumab, 14D3 antibody is assessed for its ability to detect PD-L1 expression in patients dosed with Atezolizumab in order to monitor effectiveness of therapeutic treatment.

Methods

Patients with hematological malignancies including multiple myeloma (MM), acute myeloid leukemia (AML), or myelodysplastic syndrome (MSD) is assessed for baseline expression of PD-L1 in bone marrow and blood samples. Samples are collected and processed as described in Example 2. PD-L1 expression is determined by staining with anti-PD-L1 14D3 antibody linked to a detectable label such as PE. The samples are subjected to flow cytometry to determine the baseline expression of PD-L1 in the patients. The patients are treated with Atezolizumab at a dosage regimen appropriate for the treatment of the hematological malignancy. Blood and bone marrow samples are collected at one or various time points after treatment with Atezolizumab. The samples are processed as described above and stained with anti-PD-L1 14D3 antibody linked to a detectable label (e.g., PE). Expression of PD-L1 in cells, such as live immune cells and/or tumor cells, is determined from treated patients as determined by detecting the labeled anti-PD-L1 14D3 antibody by flow cytometry.

What is claimed is:

1. An isolated anti-PD-L1 antibody, or an antigen-binding fragment thereof, wherein the antibody comprises:
   (a) a heavy chain variable region comprising:
      (i) HVR-H1 comprising the amino acid sequence TSWMN (SEQ ID NO:1);
      (ii) HVR-H2 comprising the amino acid sequence RIYPRDGDTYYNGKFKD (SEQ ID NO:2); and
      (iii) HVR-H3 comprising the amino acid sequence NPGGYYFDY (SEQ ID NO:3); and
   (b) a light chain variable region comprising:
      (i) HVR-L1 comprising the amino acid sequence RASQDIHTYLN (SEQ ID NO:4);
      (ii) HVR-L2 comprising the amino acid sequence YTSRLHS (SEQ ID NO:5); and
      (iii) HVR-L3 comprising the amino acid sequence QQVSSLPPWT (SEQ ID NO:6).

2. The antibody or antigen-binding fragment of claim 1, wherein the antibody comprises a heavy chain variable region comprising the amino acid sequence of SEQ ID NO:7, and a light chain variable region comprising the amino acid sequence of SEQ ID NO:8.

3. The antibody or antigen-binding fragment of claim 1, wherein the antibody or antigen-binding fragment does not compete with a reference antibody for binding to human PD-L1, wherein the reference antibody comprises:
   (a) a heavy chain variable region comprising:
      (i) HVR-H1 comprising the amino acid sequence GFTFSDSWIH (SEQ ID NO:11);
      (ii) HVR-H2 comprising the amino acid sequence AWISPYGGSTYYADSVKG (SEQ ID NO:12); and
      (iii) HVR-H3 comprising the amino acid sequence RHWPGGFDY (SEQ ID NO:13); and
   (b) a light chain variable region comprising:
      (i) HVR-L1 comprising the amino acid sequence RASQDVSTAVA (SEQ ID NO:14);
      (ii) HVR-L2 comprising the amino acid sequence SASFLYS (SEQ ID NO:15); and
      (iii) HVR-L3 comprising the amino acid sequence QQYLYHPAT (SEQ ID NO:16).

4. The antibody or antigen-binding fragment of claim 3, wherein the reference antibody comprises a heavy chain variable region comprising the amino acid sequence of SEQ ID NO:17, and a light chain variable region comprising the amino acid sequence of SEQ ID NO:18.

5. The antibody or antigen-binding fragment of claim 1, wherein the antibody or antigen-binding fragment is linked to a moiety.

6. The antibody or antigen-binding fragment of claim 5, wherein the moiety is a detectable moiety.

7. The antibody or antigen-binding fragment of claim 6, wherein the detectable moiety is biotin, streptavidin, a luminescent agent, an enzyme, a fluorophore, a dye, a radiolabel, a chromophore, a metal ion, a gold particle, a silver particle, a magnetic particle, a polypeptide, or an oligonucleotide.

8. An isolated nucleic acid encoding the antibody or antigen-binding fragment of claim 1.

9. A vector comprising the nucleic acid of claim 8.

10. The vector of claim 9, wherein the vector is an expression vector.

11. A host cell comprising the vector of claim 10.

12. A method of producing an anti-PD-L1 antibody or antigen-binding fragment thereof, comprising culturing the host cell of claim 11 under a condition suitable for production of the anti-PD-L1 antibody or antigen-binding fragment thereof.

13. A method for detecting PD-L1 in a biological sample obtained from a subject, the method comprising:
   (a) contacting the biological sample with the antibody or antigen-binding fragment of claim 1; and
   (b) detecting binding of the antibody or antigen-binding fragment to PD-L1 in the biological sample, thereby detecting PD-L1 in the biological sample.

14. The method of claim 13, wherein the antibody or antigen-binding fragment is detected using flow cytometry.

15. The method of claim 13, wherein the biological sample is a cell or tissue.

16. The method of claim 8, wherein the cell or tissue is a cancerous cell or cancerous tissue.

17. The method of claim 13, wherein the subject has a cancer.

18. The method of claim 17, wherein the cancer is selected from the group consisting of multiple myeloma, myelodysplastic syndrome, and acute myeloid leukemia.

19. The method of claim 13 wherein the biological sample is obtained from a subject that has been administered a therapeutic anti-PD-L1 antibody or antigen-binding fragment thereof, wherein the therapeutic antibody or antigen-binding fragment thereof comprises:
   (a) a heavy chain variable region comprising:
      (i) HVR-H1 comprising the amino acid sequence GFTFSDSWIH (SEQ ID NO:11);
      (ii) HVR-H2 comprising the amino acid sequence AWISPYGGSTYYADSVKG (SEQ ID NO:12); and
      (iii) HVR-H3 comprising the amino acid sequence RHWPGGFDY (SEQ ID NO:13); and
   (b) a light chain variable region comprising:
      (i) HVR-L1 comprising the amino acid sequence RASQDVSTAVA (SEQ ID NO:14);
      (ii) HVR-L2 comprising the amino acid sequence SASFLYS (SEQ ID NO:15); and
      (iii) HVR-L3 comprising the amino acid sequence QQYLYHPAT (SEQ ID NO:16).

20. The method of claim 19, wherein the therapeutic antibody or antigen-binding fragment thereof comprises a heavy chain variable region comprising the amino acid sequence of SEQ ID NO:17, and a light chain variable region comprising the amino acid sequence of SEQ ID NO:18.

21. A method of monitoring cancer treatment in a subject, the method comprising:
(a) contacting a first biological sample with the antibody or antigen-binding fragment of claim 1;
(b) detecting binding of the antibody or antigen-binding fragment to PD-L1 in the first biological sample;
(c) determining the amount of PD-L1 present in the first biological sample;
(d) contacting a second biological sample with the antibody or antigen-binding fragment of claim 1, wherein the second biological sample is obtained after treatment with a therapeutic anti-PD-L1 antibody or antigen-binding fragment thereof,
wherein the therapeutic antibody or antigen-binding fragment thereof comprises:
(a) a heavy chain variable region comprising:
(i) HVR-H1 comprising the amino acid sequence GFTFSDSWIH (SEQ ID NO:11);
(ii) HVR-H2 comprising the amino acid sequence AWISPYGGSTYYADSVKG (SEQ ID NO:12); and
(iii) HVR-H3 comprising the amino acid sequence RHWPGGFDY (SEQ ID NO:13); and
(b) a light chain variable region comprising:
(i) HVR-L1 comprising the amino acid sequence RASQDVSTAVA (SEQ ID NO:14);
(ii) HVR-L2 comprising the amino acid sequence SASFLYS (SEQ ID NO:15); and
(iii) HVR-L3 comprising the amino acid sequence QQYLYHPAT (SEQ ID NO:16);
(e) detecting binding of the antibody or antigen-binding fragment to PD-L1 in the second biological sample;
(f) determining the amount of PD-L1 present in the second biological sample; and
(g) comparing the amount of PD-L1 present in the first biological sample to the amount of PD-L1 present in the second biological sample.

22. The method of claim 21, wherein an increase in the amount of PD-L1 present in the second biological sample compared to the first biological sample indicates that the subject is not responding to treatment with the therapeutic anti-PD-L1 antibody.

23. The method of claim 21, wherein a decrease in the amount of PD-L1 present in the second biological sample compared to the first biological sample indicates that the subject is responding to treatment with the therapeutic anti-PD-L1 antibody.

24. The method of claim 21 wherein the first and second biological samples are cells or tissues.

25. The method of claim 24, wherein the cells or tissues are cancerous cells or cancerous tissues.

26. The method of claim 21, wherein the subject has a cancer selected from the group consisting of multiple myeloma, myelodysplastic syndrome, and acute myeloid leukemia.

27. The method of claim 21, wherein the therapeutic antibody or antigen-binding fragment thereof comprises a heavy chain variable region comprising the amino acid sequence of SEQ ID NO:17, and a light chain variable region comprising the amino acid sequence of SEQ ID NO:18.

28. The method of claim 13, wherein the subject is a human.

29. A composition comprising the antibody or antigen-binding fragment of claim 1.

30. A kit for detecting PD-L1 in a biological sample comprising the antibody of claim 1.

31. The antibody or antigen-binding fragment of claim 6, wherein the detectable moiety is a fluorophore.

32. The antibody or antigen-binding fragment of claim 2, wherein the antibody or antigen-binding fragment is linked to a moiety.

33. The antibody or antigen-binding fragment of claim 32, wherein the moiety is a detectable moiety.

34. The antibody or antigen-binding fragment of claim 33, wherein the detectable moiety is biotin, streptavidin, a luminescent agent, an enzyme, a fluorophore, a dye, a radiolabel, a chromophore, a metal ion, a gold particle, a silver particle, a magnetic particle, a polypeptide, or an oligonucleotide.

35. The antibody or antigen-binding fragment of claim 33, wherein the detectable moiety is a fluorophore.

36. An isolated nucleic acid encoding the antibody or antigen-binding fragment of claim 2.

37. A vector comprising the nucleic acid of claim 36.

38. The vector of claim 37, wherein the vector is an expression vector.

39. A host cell comprising the vector of claim 38.

40. A method of producing an anti-PD-L1 antibody or antigen-binding fragment thereof, comprising culturing the host cell of claim 39 under a condition suitable for production of the anti-PD-L1 antibody or antigen-binding fragment thereof.

41. A method for detecting PD-L1 in a biological sample obtained from a subject, the method comprising:
(a) contacting the biological sample with the antibody or antigen-binding fragment of claim 2; and
(b) detecting binding of the antibody or antigen-binding fragment to PD-L1 in the biological sample, thereby detecting PD-L1 in the biological sample.

42. The method of claim 41 wherein the biological sample is obtained from a subject that has been administered a therapeutic anti-PD-L1 antibody or antigen-binding fragment thereof, wherein the therapeutic antibody or antigen-binding fragment thereof comprises:
(a) a heavy chain variable region comprising:
(i) HVR-H1 comprising the amino acid sequence GFTFSDSWIH (SEQ ID NO:11);
(ii) HVR-H2 comprising the amino acid sequence AWISPYGGSTYYADSVKG (SEQ ID NO:12); and
(iii) HVR-H3 comprising the amino acid sequence RHWPGGFDY (SEQ ID NO:13); and
(b) a light chain variable region comprising:
(i) HVR-L1 comprising the amino acid sequence RASQDVSTAVA (SEQ ID NO:14);
(ii) HVR-L2 comprising the amino acid sequence SASFLYS (SEQ ID NO:15); and
(iii) HVR-L3 comprising the amino acid sequence QQYLYHPAT (SEQ ID NO:16).

43. The method of claim 42, wherein the therapeutic antibody or antigen-binding fragment thereof comprises a heavy chain variable region comprising the amino acid sequence of SEQ ID NO:17, and a light chain variable region comprising the amino acid sequence of SEQ ID NO:18.

44. A method of monitoring cancer treatment in a subject, the method comprising:
(a) contacting a first biological sample with the antibody or antigen-binding fragment of claim 2;
(b) detecting binding of the antibody or antigen-binding fragment to PD-L1 in the first biological sample;
(c) determining the amount of PD-L1 present in the first biological sample;

(d) contacting a second biological sample with the antibody or antigen-binding fragment of claim 1, wherein the second biological sample is obtained after treatment with a therapeutic anti-PD-L1 antibody or antigen-binding fragment thereof,
wherein the therapeutic antibody or antigen-binding fragment thereof comprises:
(a) a heavy chain variable region comprising:
(i) HVR-H1 comprising the amino acid sequence GFTFSDSWIH (SEQ ID NO:11);
(ii) HVR-H2 comprising the amino acid sequence AWISPYGGSTYYADSVKG (SEQ ID NO:12); and
(iii) HVR-H3 comprising the amino acid sequence RHWPGGFDY (SEQ ID NO:13); and
(b) a light chain variable region comprising:
(i) HVR-L1 comprising the amino acid sequence RASQDVSTAVA (SEQ ID NO:14);
(ii) HVR-L2 comprising the amino acid sequence SASFLYS (SEQ ID NO:15); and
(iii) HVR-L3 comprising the amino acid sequence QQYLYHPAT (SEQ ID NO:16);
(e) detecting binding of the antibody or antigen-binding fragment to PD-L1 in the second biological sample;
(f) determining the amount of PD-L1 present in the second biological sample; and
(g) comparing the amount of PD-L1 present in the first biological sample to the amount of PD-L1 present in the second biological sample.

45. The method of claim 44, wherein an increase in the amount of PD-L1 present in the second biological sample compared to the first biological sample indicates that the subject is not responding to treatment with the therapeutic anti-PD-L1 antibody.

46. The method of claim 44, wherein a decrease in the amount of PD-L1 present in the second biological sample compared to the first biological sample indicates that the subject is responding to treatment with the therapeutic anti-PD-L1 antibody.

47. The method of claim 44, wherein the therapeutic antibody or antigen-binding fragment thereof comprises a heavy chain variable region comprising the amino acid sequence of SEQ ID NO:17, and a light chain variable region comprising the amino acid sequence of SEQ ID NO:18.

48. The method of claim 41, wherein the subject is a human.

49. A composition comprising the antibody or antigen-binding fragment of claim 2.

50. The antibody or antigen-binding fragment of claim 1, wherein the antibody comprises a heavy chain comprising the amino acid sequence of SEQ ID NO:9, and a light chain comprising the amino acid sequence of SEQ ID NO:10.

51. The antibody or antigen-binding fragment of claim 50, wherein the antibody or antigen-binding fragment is linked to a moiety.

52. The antibody or antigen-binding fragment of claim 51, wherein the moiety is a detectable moiety.

53. The antibody or antigen-binding fragment of claim 52, wherein the detectable moiety is biotin, streptavidin, a luminescent agent, an enzyme, a fluorophore, a dye, a radiolabel, a chromophore, a metal ion, a gold particle, a silver particle, a magnetic particle, a polypeptide, or an oligonucleotide.

54. The antibody or antigen-binding fragment of claim 52, wherein the detectable moiety is a fluorophore.

55. An isolated nucleic acid encoding the antibody or antigen-binding fragment of claim 50.

56. A vector comprising the nucleic acid of claim 55.

57. The vector of claim 56, wherein the vector is an expression vector.

58. A host cell comprising the vector of claim 55.

59. A method of producing an anti-PD-L1 antibody or antigen-binding fragment thereof, comprising culturing the host cell of claim 58 under a condition suitable for production of the anti-PD-L1 antibody or antigen-binding fragment thereof.

60. A method for detecting PD-L1 in a biological sample obtained from a subject, the method comprising:
(a) contacting the biological sample with the antibody or antigen-binding fragment of claim 50; and
(b) detecting binding of the antibody or antigen-binding fragment to PD-L1 in the biological sample, thereby detecting PD-L1 in the biological sample.

61. The method of claim 60 wherein the biological sample is obtained from a subject that has been administered a therapeutic anti-PD-L1 antibody or antigen-binding fragment thereof, wherein the therapeutic antibody or antigen-binding fragment thereof comprises:
(a) a heavy chain variable region comprising:
(i) HVR-H1 comprising the amino acid sequence GFTFSDSWIH (SEQ ID NO:11);
(ii) HVR-H2 comprising the amino acid sequence AWISPYGGSTYYADSVKG (SEQ ID NO:12); and
(iii) HVR-H3 comprising the amino acid sequence RHWPGGFDY (SEQ ID NO:13); and
(b) a light chain variable region comprising:
(i) HVR-L1 comprising the amino acid sequence RASQDVSTAVA (SEQ ID NO:14);
(ii) HVR-L2 comprising the amino acid sequence SASFLYS (SEQ ID NO:15); and
(iii) HVR-L3 comprising the amino acid sequence QQYLYHPAT (SEQ ID NO:16).

62. The method of claim 61, wherein the therapeutic antibody or antigen-binding fragment thereof comprises a heavy chain variable region comprising the amino acid sequence of SEQ ID NO:17, and a light chain variable region comprising the amino acid sequence of SEQ ID NO:18.

63. A method of monitoring cancer treatment in a subject, the method comprising:
(a) contacting a first biological sample with the antibody or antigen-binding fragment of claim 50;
(b) detecting binding of the antibody or antigen-binding fragment to PD-L1 in the first biological sample;
(c) determining the amount of PD-L1 present in the first biological sample;
(d) contacting a second biological sample with the antibody or antigen-binding fragment of claim 1, wherein the second biological sample is obtained after treatment with a therapeutic anti-PD-L1 antibody or antigen-binding fragment thereof,
wherein the therapeutic antibody or antigen-binding fragment thereof comprises:
(a) a heavy chain variable region comprising:
(i) HVR-H1 comprising the amino acid sequence GFTFSDSWIH (SEQ ID NO:11);
(ii) HVR-H2 comprising the amino acid sequence AWISPYGGSTYYADSVKG (SEQ ID NO:12); and
(iii) HVR-H3 comprising the amino acid sequence RHWPGGFDY (SEQ ID NO:13); and (b) a light chain variable region comprising:
  (i) HVR-L1 comprising the amino acid sequence RASQDVSTAVA (SEQ ID NO:14);
  (ii) HVR-L2 comprising the amino acid sequence SASFLYS (SEQ ID NO:15); and
  (iii) HVR-L3 comprising the amino acid sequence QQYLYHPAT (SEQ ID NO:16);
(e) detecting binding of the antibody or antigen-binding fragment to PD-L1 in the second biological sample;
(f) determining the amount of PD-L1 present in the second biological sample; and
(g) comparing the amount of PD-L1 present in the first biological sample to the amount of PD-L1 present in the second biological sample.

64. The method of claim 63, wherein an increase in the amount of PD-L1 present in the second biological sample compared to the first biological sample indicates that the subject is not responding to treatment with the therapeutic anti-PD-L1 antibody.

65. The method of claim 63, wherein a decrease in the amount of PD-L1 present in the second biological sample compared to the first biological sample indicates that the subject is responding to treatment with the therapeutic anti-PD-L1 antibody.

66. The method of claim 63, wherein the therapeutic antibody or antigen-binding fragment thereof comprises a heavy chain variable region comprising the amino acid sequence of SEQ ID NO:17, and a light chain variable region comprising the amino acid sequence of SEQ ID NO:18.

67. The method of claim 60, wherein the subject is a human.

68. A composition comprising the antibody or antigen-binding fragment of claim 50.

* * * * *